(12) United States Patent
Muller

(10) Patent No.: US 8,237,835 B1
(45) Date of Patent: Aug. 7, 2012

(54) CONFOCAL IMAGING DEVICE USING SPATIALLY MODULATED ILLUMINATION WITH ELECTRONIC ROLLING SHUTTER DETECTION

(75) Inventor: Matthew Stefan Muller, Bloomington, IN (US)

(73) Assignee: Aeon Imaging, LLC, Bloomington, IN (US)

( * ) Notice: Subject to any disclaimer, the term of this patent is extended or adjusted under 35 U.S.C. 154(b) by 0 days.

(21) Appl. No.: 13/302,814

(22) Filed: Nov. 22, 2011

Related U.S. Application Data

(60) Provisional application No. 61/488,145, filed on May 19, 2011, provisional application No. 61/496,666, filed on Jun. 14, 2011.

(51) Int. Cl.
*H04N 3/14* (2006.01)
*H04N 5/335* (2006.01)
*H04N 7/18* (2006.01)
*G06K 9/00* (2006.01)
*G01J 1/20* (2006.01)
*A61B 3/10* (2006.01)

(52) U.S. Cl. ....... 348/296; 348/78; 382/128; 250/201.9; 351/214

(58) Field of Classification Search .............. 348/78, 348/77, 296; 382/117; 250/201.9; 351/206, 351/214, 215; 600/452
See application file for complete search history.

(56) References Cited

U.S. PATENT DOCUMENTS

| | | | | |
|---|---|---|---|---|
| 5,028,802 A | * | 7/1991 | Webb et al. | 250/235 |
| 5,563,710 A | * | 10/1996 | Webb et al. | 356/445 |
| 5,587,832 A | * | 12/1996 | Krause | 359/385 |
| 5,867,251 A | | 2/1999 | Webb | |
| 5,923,466 A | | 7/1999 | Krause et al. | |
| 6,121,603 A | * | 9/2000 | Hang et al. | 250/216 |
| 6,399,936 B1 | * | 6/2002 | Hang et al. | 250/216 |
| 6,483,641 B1 | * | 11/2002 | MacAulay | 359/385 |
| 6,572,230 B2 | * | 6/2003 | Levine | 351/221 |
| 7,057,806 B2 | * | 6/2006 | Atkinson | 359/368 |
| 7,331,669 B2 | * | 2/2008 | Elsner | 351/206 |
| 7,335,898 B2 | | 2/2008 | Donders et al. | |
| 7,350,920 B2 | * | 4/2008 | Levine | 351/206 |
| 7,755,832 B2 | | 7/2010 | MacAulay | |
| 7,831,106 B2 | | 11/2010 | Elsner et al. | |
| 2006/0017001 A1 | * | 1/2006 | Donders et al. | 250/390.07 |
| 2007/0273784 A1 | * | 11/2007 | Neil et al. | 348/362 |

(Continued)

FOREIGN PATENT DOCUMENTS

WO   WO 2007113473 A1 * 10/2007

OTHER PUBLICATIONS

Chia-Kai Liang et al., "Analysis and Compensation of Rolling Shutter Effect," Image Processing, IEEE Transactions on, vol. 17, Issue 8, Aug. 2008, pp. 1323-1330.

(Continued)

*Primary Examiner* — John Villecco
(74) *Attorney, Agent, or Firm* — Taft Stettinius & Hollister LLP; Ryan O. White

(57) ABSTRACT

A digital imaging device comprising a light source, a pixel array detector having a rolling shutter functionality, a spatial light modulator configured to produce one or more modulation patterns during a frame exposure of the pixel array detector, and at least one timing signal configured to control a spatial-temporal relationship between a rolling shutter of the pixel array detector and the one or more modulation patterns provided by the spatial light modulator.

23 Claims, 13 Drawing Sheets

U.S. PATENT DOCUMENTS

| | | | |
|---|---|---|---|
| 2009/0218527 A1* | 9/2009 | French et al. | 250/578.1 |
| 2009/0244482 A1* | 10/2009 | Elsner et al. | 351/206 |
| 2010/0007849 A1* | 1/2010 | Liesfeld et al. | 351/207 |
| 2010/0128221 A1* | 5/2010 | Muller et al. | 351/207 |
| 2011/0187878 A1* | 8/2011 | Mor et al. | 348/218.1 |

OTHER PUBLICATIONS

J.-B. Chun, et al.,"Suppressing Rolling-Shutter Distortion of CMOS Image Sensors by Motion Vector Detection," IEEE Transactions on Consumer Electronics, pp. 1479-1487, Nov. 2008.

Won-Ho Cho, et al., "CMOS Digital Image Stabilization," IEEE Transactions on Consumer Electronics, vol. 53 Issue: 3 (2007) pp. 979-986.

Ait-Aider, et al., "Simultaneous Object Pose and Velocity Computation Using a Single View from a Rolling Shutter Camera," ECCV 2006, 3952, pp. 56-68 (2006).

Kodak, "Shutter Operations for CCD and CMOS Image Sensors," Eastman Kodak Company Application Note Revision 2.0 MTD/PS-0259 (2003).

Hanley QS, et al., "An optical sectioning programmable array microscope implemented with a digital micromirror device," Journal of Microscopy, 1999. 196(3): p. 317-331.

Mico, et al., "Single-step superresolution by interferometric imaging," Opt. Express 12, 2589-2596 (2004).

Park, et al., "Frequency domain depth filtering of integral imaging," Opt. Express 19, 18729-18741 (2011).

Cotte, et al., "Beyond the lateral resolution limit by phase imaging," Journal of Biomedical Optics, vol. 16, No. 10, p. 106007-1, 2011.

Grajciar, et al., "Parallel Fourier domain optical coherence tomography for in vivo measurement of the human eye," Opt. Express 13, 1131-1137 (2005).

Grajciar, et al., "High sensitivity phase mapping with parallel Fourier domain optical coherence tomography at 512 000 A-scan/s," Opt. Express 18, 21841-21850 (2010).

A. Barty, et al., "Quantitative optical phase microscopy," Opt. Lett. 23, 817-819 (1998).

PH Tomlins, "Theory, developments and applications of optical coherence tomography", J. Phys. D: Appl. Phys., vol. 38 pp. 2519-2535 (2005).

Zysk, et al., "Optical coherence tomography: a review of clinical application development from bench to bedside," Journal of Biomedical Optics 12(5), 051403 (2007).

Quan, et al., "Shape measurement of small objects using LCD fringe projection with phase shifting," Opt. Commun. 189, pp. 21-29 (2001).

McIntyre, et al., "Quantitative SLM-Based Differential Interference Contrast Imaging," Opt. Exp. 18, pp. 14063-14078 (2010).

Drexler, et al., "State-of-the art retinal optical coherence tomography," Prog. Ret. Eye Res. 27, pp. 45-88 (2008).

Fukano, et al., "Whole-field fluorescence microscope with digital micromirror device: imaging of biological samples," Appl. Opt. 42, pp. 4119-4124 (2003).

Hillman, et al., "High-resolution, wide-field object reconstruction with synthetic aperture Fourier holographic optical microscopy," Opt. Exp. 17, 7873-7892 (2009).

Sun, et al., "3D In Vivo optical coherence tomography based on a low-voltage, large-scan-range 2D MEMS mirror," Opt. Express 18, 12065-12075 (2010).

A. Ponticorvo, et al., "Simultaneous imaging of oxygen tension and blood flow in animals using a digital micromirror device," Opt. Exp. 18, pp. 8160-8170 (2010).

Walther et al, "Effects of axial, transverse, and oblique sample motion in FD OCT in systems with global or rolling shutter line detector," J. Opt. Soc. Am., pp. 2791 (2008).

A. F. Fercher et al., "Optical coherence tomography—principles and applications," Rep. Prog. Phys, 66, 239-303 (2003).

Jeong, et al, "Fourier-domain holographic optical coherence imaging of tumor spheroids and mouse eye," Appl. Opt. 44, 1798-1805 (2005).

Schausberger, et al, "Flexible contrast for low-coherence interference microscopy by Fourier-plane filtering with a spatial light modulator," Opt. Lett. 35, 4154-4156 (2010).

Liu, et al, "Dual-frequency pattern scheme for high-speed 3-D shape measurement," Opt. Express 18, 5229-5244 (2010).

F. Le Clerc, et al, "Synthetic-aperture experiment in the visible with on-axis digital heterodyne holography," Opt. Lett. 26, 1550-1552 (2001).

Ferguson, et al, "Adaptive optics scanning laser ophthalmoscope with integrated wide-field retinal imaging and tracking," J. Opt. Soc. Am. A 27, A265-A277 (2010).

Lin An, et al., "High speed spectral domain optical coherence tomography for retinal imaging at 500,000 A-lines per second," Biomed. Opt. Express 2, 2770-2783 (2011).

Neil, et al., "Method of obtaining optical sectioning by using structured light in a conventional microscope," Opt. Lett. 22, 1905-1907 (1997).

Jiang, et al., "Differential high-speed digital micromirror device based fluorescence speckle confocal microscopy," Appl. Opt. 49, 497-504 (2010).

Delica, et al., "Wide-field depth-sectioning fluorescence microscopy using projector-generated patterned illumination," Appl. Opt. 46, 7237-7243 (2007).

K. M. Hampson, et al., Topical Review: Adaptive optics and vision, J. Mod. Opt. 55, pp. 3423-3465 (2008).

Sung, et al., "Optical Diffraction Tomography for High Resolution Live Cell Imaging," Opt. Exp. 17, 266-277 (2009).

Zara, et al., "Electrostatic micromachine scanning mirror for optical coherence tomography," Opt. Lett. 28, 628-630 (2003).

Bednarkiewicz, et al., "Digital micromirror device as a spatial illuminator for fluorescence lifetime and hyperspectral imaging," Appl. Opt. 47, 1193-1199 (2008).

Alexandrov, et al., "Synthetic Aperture Fourier Holographic Optical Microscopy,"., Phys. Rev. Lett. 97, pp. 168102-1 (2006).

Ayubi, et al,, "Three-dimensional profiling with binary fringes using phase-shifting interferometry algorithms," Appl. Opt. 50, 147-154 (2011).

Verveer, et al., "Theory of confocal fluorescence imaging in the programmable array microscope (PAM)," J. Micros. 189, pp. 192-198 (1997).

Schwarz, et al., "Imaging interferometric microscopy," Opt. Lett. 28, 1424-1426 (2003).

R. Heintzmann, "Structured Illumination Methods," from *Handbook of Biological Confocal Microscopy, 3rd ed.*, J. B. Pawley ed., Ch. 13 pp. 265-277 (2006).

T. J. Holmes, D. Biggs, et al., "Blind Deconvolution," from *Handbook of Biological Confocal Microscopy, 3rd ed.*, J. B. Pawley ed., Ch. 24 pp. 473-475 (2006).

* cited by examiner

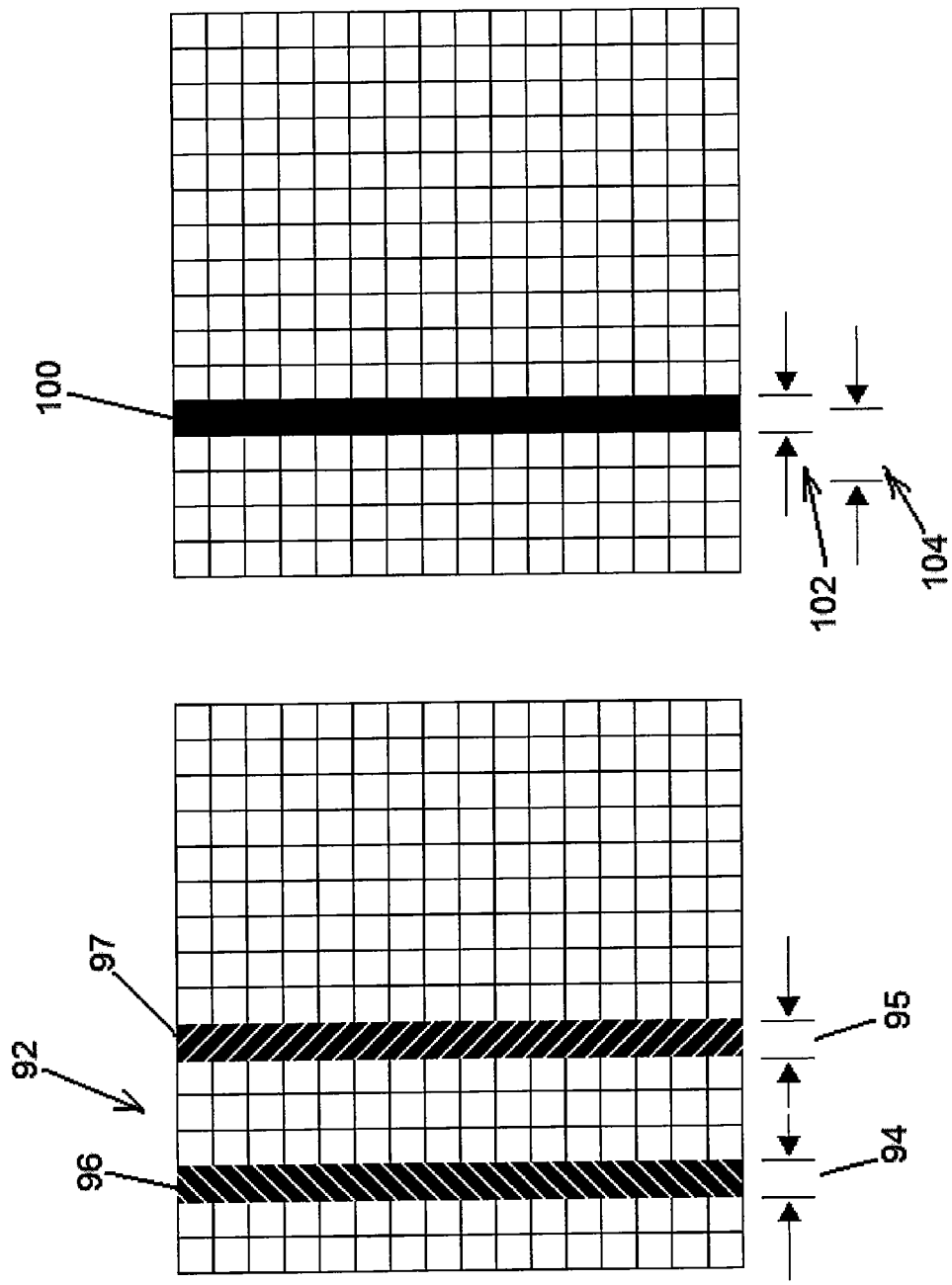

CONFOCAL IMAGING DEVICE USING SPATIALLY MODULATED ILLUMINATION WITH ELECTRONIC ROLLING SHUTTER DETECTION

CROSS-REFERENCE TO RELATED APPLICATIONS

This application is related and claims priority to U.S. Provisional Patent Application Ser. No. 61/488,145 filed on May 19, 2011 and U.S. Provisional Patent Application Ser. No. 61/496,666 filed on Jun. 14, 2011. The complete and entire disclosures for both of these respective applications are hereby expressly incorporated herein by this reference.

This invention was made in part with government support under grant reference number 4R44EY020017-02 awarded by the National Eye Institute. The Government therefore has certain rights in this invention.

BACKGROUND OF THE INVENTION

Confocal imaging is a well-known imaging technique in which light scattered from a target is spatially filtered before it is detected. Spatial filtering can reduce image artifacts such as unwanted scattering and reflections from either the target or components within the imaging device, and can provide improved image contrast, as well as isolate features of interest. Confocal imaging devices have been designed and implemented for a wide variety of microscopy, dark-field, fluorescence, polarization sensitive, nonlinear optical, interferometric, and ophthalmic imaging applications.

In a laser scanning confocal imaging system, the illumination light is focused to a point or line and scanned across the target to obtain an image of the entire field of view. Light scattered from the target is typically descanned using the same scanning element and directed through an aperture to a photosensitive detector. By synchronizing the scanning with the exposure timing of the detector, a two-dimensional image of the target can be constructed. The insertion of an aperture at a plane conjugate to the target restricts the amount of out-of-focus light that can reach the detector. Laser scanning confocal imaging systems have been adapted for retinal imaging in scanning laser ophthalmoscopes, and for three-dimensional interferometric imaging in optical coherence tomography devices.

U.S. Pat. No. 7,831,106 proposes the use of a laser scanning confocal imaging system without descanning. In this design, a confocal aperture is created by an electronic rolling shutter detection means on a two-dimensional pixel array sensor. During each frame, the rolling shutter progressively scans in one-dimension across the active sensor region with a shutter width related to the total frame exposure time. At each shutter position, the pixel values along the length of the shutter are obtained by integrating the charge accumulated across only the width of the shutter. Light incident on the sensor outside the rolling shutter width is not captured.

The electronic rolling shutter is a fundamentally different form of detection than a global shutter, which integrates charge across the entire active area during the exposure time. Charge coupled device (CCD) sensors are an example of a global shutter sensor; many complementary metal-oxide semiconductor (CMOS) sensors use rolling shutter technology, though they are now also available with global shutters. In non-confocal imaging applications, rolling shutter sensors are commonly used in the place of a global shutter sensor due to the low cost of CMOS technology. In these cases, a rolling shutter is generally considered a detriment to imaging performance since target motion in the same or opposite direction of the rolling shutter will appear distorted. Several research groups have investigated post-processing techniques to reduce motion blur and other distortions in non-confocal cameras that use rolling shutter sensors.

The confocal imaging system design proposed by U.S. Pat. No. 7,831,106 scans an illumination line across the target in synchrony with the rolling shutter detection of a sensor placed at a conjugate target plane. This approach allows the aperture width to be adjusted electronically in real-time, and permits an operator to adjust the trade-off between the amounts of light detected and confocal spatial filtering for a given target. Furthermore, the relative timing between the shutter position and scanning angle can be adjusted electronically in real-time in order to perform dark-field imaging. When the frequency or polarization components of the light are spatially separated, the rolling shutter can also be used to filter the frequency or polarization of the light scattered from the target.

The use of the electronic rolling shutter as a confocal aperture permits adjustments to the aperture position and width in pixel increments. Compared to mechanical apertures, the use of the rolling shutter as a confocal aperture is a cost-effective approach that permits rapid, quantifiable, accurate and reliable adjustments. However, U.S. Pat. No. 7,831,106 requires the formation of a slit that is scanned across the field of view of the target. With a single scanner, the simultaneous illumination of a target with a second spatially offset slit, or other more complex patterns, requires additional illumination pathways to the scanner. These illumination pathways are difficult to align with high precision and each enable only a few additional illumination geometry configurations. A confocal imaging method and device that further provides flexible and precise electronically-controlled real-time adjustments to the illumination geometry using a common illumination pathway and that is compact, robust, reliable, and cost-effective would be appreciated.

In a programmable array microscope (PAM) confocal imaging system, the illumination pattern incident on the target is adjustable using a spatial light modulator, such as a digital micromirror array or liquid crystal display. In this configuration, a confocal image is constructed from multiple frames that are acquired while the target is illuminated with a series of alternating dot lattice or pseudo-random patterns. The light returning from the target is spatially filtered by the spatial light modulator and global shutter CCD; only the sensor pixels conjugate to the "on" pixels of the micromirror array are used to construct the final image. A laser contrast speckle imaging system with a spatial light modulator and CMOS sensor has been reported that measures blood flow changes. This system uses a spatial light modulator frame rate that is many times slower than that of the sensor. This prevents the spatial light modulator from rapidly projecting a sequence of narrow illumination lines that could continuously overlap with the rolling shutter during a single frame. Furthermore, as reported, this system does not use the rolling shutter of the CMOS sensor as a confocal aperture; the CMOS sensor could be substituted for a global shutter CCD and achieve substantially the same performance.

PAM systems for fluorescent microscopy have been implemented using two pixel array detectors to collect both the in-focus and out-of-focus light that scatters from a target. In these systems, the "off" and "on" angular orientation of the micromirror array elements is used to direct the light scattered from the target to each of the two detectors. A fluorescence-based PAM has also been implemented in which the scattered light is spatially filtered with a fiber optic cable and measured using a spectrometer for hyperspectral and fluorescence lifetime imaging.

The ability of spatial light modulators to rapidly change the modulation pattern used to illuminate an object makes them well-suited for structured light illumination applications, such as phase measuring profilometry and fringe-projection microscopy, in which a series of images taken with periodic illumination fringes can be used to perform spatial filtering. In these systems, confocal imaging is achieved with a global shutter CCD sensor. The use of a spatial light modulator is particularly attractive due to its ability to change the frequency and shape of the structured light illumination in real time. Although spatial light modulators are unable to continuously scan a beam of light across a sample, they can simulate the effect by rapidly projecting a series of modulation patterns.

The use of a digital micromirror array in a PAM system has attracted interest due to its low cost, illumination pattern flexibility, high mirror speed, and ever-increasing pixel resolution. However, the use of a series of illumination patterns to construct a confocal image requires the acquisition of multiple frames, during which time the imaging system is highly sensitive to motion artifacts. U.S. Pat. No. 5,923,466 addresses this difficulty by proposing a dual-pass system, in which the light returning from the target is directed back through the spatial light modulator prior to being detected. This approach is similar to the laser scanning designs discussed above. While dual-pass designs have been proven effective for confocal imaging, they typically require a beam separating element between the scanning component and the source to direct the light return from the target to the detector. In a confocal dual-pass spatial light modulator system, the addition of a beam separating element and optical design of the associated detection pathway prevents the use of a fully integrated illumination source and micromirror array, as provided in digital light projectors. Therefore, a method and device for confocal imaging that enables the use of cost effective and robust spatial light modulators that are integrated with the illumination source, such as currently available compact and lightweight digital light projectors, which can be handheld, would be appreciated. A method and device for confocal imaging that further removes the need to construct a confocal image using multiple sensor frames, as in fringe-projection microscopy, would also be appreciated.

U.S. Pat. Nos. 5,867,251 and 7,755,832 propose the implementation of a second spatial light modulator, driven in tandem with the first, to act as a second aperture and to restrict the light returning from the target that reaches the detector. This approach results in a complex system that requires precise alignment and timing control of the spatial light modulators; such a system has not, to the present inventors' knowledge, been reduced to practice and reported in the literature. A method and device that provides flexible, cost-effective, and robust aperture control in a PAM system would be appreciated.

Optical coherence tomography (OCT) based systems perform imaging by analyzing the interference between broadband light returning from a target and light reflected in a reference arm with a known path delay. The most common implementation uses a Michelson interferometer, and determines the backscattered intensity with respect to sample depth at one transverse point on the sample at a time. A three-dimensional image is built up by raster scanning the beam across the sample. Numerous comprehensive reviews of the progress and development of OCT-based systems and their applications can be found in the literature.

OCT systems broadly belong to two classes: time-domain OCT and frequency-domain OCT. The frequency-domain OCT class is further separated into spectral-domain OCT (SD-OCT) and swept source OCT (SS-OCT) design architectures. Spectral-domain and swept source OCT are commonly also referred to as Fourier-domain OCT and optical frequency domain imaging, respectively, by those skilled in the art.

In the case of time-domain OCT, the reference path delay is commonly mechanically stepped across the full sample depth range. At each reference arm position, the intensity of the interference is recorded by a photodetector, yielding the scattering depth profile for the reference arm range of motion. The speed at which the reference path delay can be mechanically scanned typically limits the acquisition rate. Although time-domain OCT can rapidly provide en face images of the target at a single depth position, time-domain OCT suffers from poorer sensitivity as compared to the class of frequency-domain OCT systems.

In SS-OCT systems, the illumination source is a tunable laser with a narrow instantaneous bandwidth. An axial scan is constructed by sweeping the frequency of the laser through its gain bandwidth while measuring the interference signal intensity.

In SD-OCT systems, the reference arm remains fixed, and the light from the reference and sample arms is measured with a spectrometer, commonly comprised of a fixed grating and a line-scan sensor. An inverse Fourier transform is applied in post-processing to reconstruct the scattering depth profile, achieving the same axial resolution as obtained in time-domain OCT systems. The electronic line-scan sensor provides a faster scan rate than the mechanical mirror scan rates achieved in TD-OCT. In addition, by spreading the imaging spectrum across many pixels, the noise is reduced, permitting a higher sensitivity with respect to TD-OCT. However, the use of a single sensor in SD-OCT makes these systems more susceptible to random intensity noise than swept-source and time-domain OCT systems that use a pair of photodetectors for balanced detection.

Each of the above OCT systems typically use a broad bandwidth source to achieve a high depth resolution and a pair of galvanometer scanners to quickly raster scan a spot over the target. Spatial light modulators, such as digital micromirror arrays, have been used in catheter-based OCT applications where their small size is an advantage. In these systems, the light returning from the target is descanned prior to detection.

The amount of reference arm light used in an OCT system is typically adjusted using a partial reflector or other variable attenuator depending on the target being imaged. To maximize the dynamic range of the system, the reference arm power is increased until the light detected at all points on the target is just below saturation. When there are differences in the intensity of light return across the field of view of the target, the noise floor of the imaging system can be limited by the dynamic range of the sensor's analog to digital converter, rather than the sensitivity limit caused by either the shot or dark noise.

Line-scanning parallel SD-OCT systems have been reported that use a two-dimensional detector and illuminate the target with a line. In these systems, the light returning from the target is descanned and sent through a linear aperture to reject light outside the illumination focal volume. During detection, one axis of the two dimensional sensor represents the frequency of the interferogram, while the other is the lateral position along the target. An advantage of parallel SD-OCT systems is the simultaneous acquisition of depth and lateral scans during each frame exposure, permitting an increase in imaging speed.

A method and device for OCT imaging that enables the use of an illumination source integrated with a spatial light modulator, combined with a confocal rolling shutter means of detection, would be appreciated. Specifically, the use of an integrated source and spatial light modulator, such as a compact and lightweight digital light projector, which can be handheld, would be more compact and cost-effective than existing OCT designs. The modification of the illumination modulation pattern to reduce differences in the intensity of light return across the field of view of the target, and thereby increase the dynamic range of the image, would be appreciated.

Adaptive optics (AO) imaging systems strive to correct aberrations in the detected light to produce higher resolution and higher contrast images. AO has been extensively used in biomedical imaging, microscopy and for imaging structures in the ocular fundus in animals and humans.

AO imaging systems typically measure and correct for wavefront aberrations in the light returning from the target. Wavefront aberrations are measured using a wavefront detector in a conjugate Fourier plane, such as a Shack-Hartmann sensor, which consists of a lenslet array and global shutter 2-dimensional pixel array detector. Feedback from the Shack-Hartmann wavefront detector is used to drive one or more wavefront controllers, typically deformable mirrors or liquid crystal spatial light modulators. A scanning laser opthalmoscope AO system using a woofer-tweeter set of deformable mirrors for coarse and fine wavefront adjustments over a wide field of view has been demonstrated with retinal tracking.

To minimize unwanted aberrations, ophthalmic AO systems typically require a large amount of space, with separate conjugate pupil planes required for the horizontal scanner, vertical scanner, wavefront detector, and wavefront controller. To the present inventor's knowledge, all ophthalmic scanning laser AO systems have performed de-scanning prior to detecting and modifying the wavefront. A more compact AO imaging device that uses cost effective and robust spatial light modulators that are integrated with the illumination source, such as currently available compact and lightweight digital light projectors, which can be handheld, would be appreciated. A method and device for AO imaging that could illuminate selected target locations suitable for obtaining accurate wavefront detection measurements, correct optical aberrations, and image those target locations that would otherwise return poorer image contrast, image focus, or less spatially filtered light, would be appreciated. A method and device for AO imaging that uses the spatial filtering properties of a cost-effective rolling shutter sensor for detecting changes in the wavefront would be appreciated.

Optical synthetic aperture imaging systems take multiple measurements of a target from varied detection angles and interfere the returning wavefront with a reference beam to gain amplitude and phase information of the light returning from the target. By introducing the reference beam at a large off-axis angle with respect to the angle of light returning from the target, the spatial frequency content is downshifted, permitting enhanced image resolution, depth of focus, field of view and working distance. A similar approach, with detection in the Fourier plane of the target, has reported relaxed constraints on the attainable field of view for a given number of pixels in the detector array. Another reported approach records a series of holograms after spatially filtering the light returning from the target in the Fourier plane.

One application of synthetic aperture imaging has been for use in microscopy, where the technique enables high resolution imaging with lower numerical aperture optics. A device and method to illuminate a target with a specific range or set of angles under real-time software control would be appreciated. A device and method that spatially filters the light returning from the target according to a specific angle, and allows flexible, reproducible and accurate setting and control of the angle of detection with respect to the angle of illumination would be appreciated. A device and method that performs synthetic aperture retinal imaging as a more cost-effective and compact alternative to adaptive optics imaging would be appreciated.

The present invention is intended to improve upon and resolve some of these known deficiencies within the relevant art.

SUMMARY OF THE INVENTION

The present invention relates to a confocal imaging device and method that uses a spatial light modulator to illuminate a target with an illumination pattern, together with a two-dimensional pixel array sensor with rolling shutter functionality to spatially filter the light return from the target. At least one timing signal controls the spatial-temporal relationship between the confocal aperture created by the rolling shutter and modulation pattern provided by the spatial light modulator. In specific embodiments, the imaging device comprises a light source, a pixel array detector having a rolling shutter functionality, a spatial light modulator configured to produce one or more modulation patterns during a frame exposure of the pixel array detector, and at least one timing signal configured to control a spatial-temporal relationship between a rolling shutter of the pixel array detector and the one or more modulation patterns provided by the spatial light modulator.

According to one embodiment, a compact and lightweight digital light projector, which can be handheld is used as an integrated source and a spatial light modulator, which enables the imaging system to be smaller in size, lower in cost (as compared to existing scanning laser confocal imaging devices), as well as easier to align, calibrate and control. Other embodiments include design adaptations commonly known to those skilled in the art to perform fluorescence, polarization-sensitive, dark-field, fringe contrast, fringe projection, synthetic aperture, holographic, diffractive, Fourier, spectroscopic, and interferometric-based imaging, in microscope and ophthalmoscope configurations.

In accordance with specific illustrative embodiments, a digital imaging method is performed by illuminating a spatial light modulator with one or more light source such that the illuminated spatial light modulator produces one or more modulation patterns during a frame exposure of a pixel array detector having a rolling shutter functionality. The resulting one or more modulation patterns is directed onto a target and light from the target is directed to the pixel array detector. At least one timing signal is used to control a spatial-temporal relationship between a rolling shutter of the pixel array detector and the one or more modulation patterns provided by the spatial light modulator.

In one embodiment of the present invention, the illumination source and spatial light modulator produce a series of lines parallel to the rolling shutter in rapid succession across the field of view of the target, and the timing of the illumination pattern is matched to that of the rolling shutter at a conjugate image plane. This embodiment uses the rolling shutter confocal aperture to allow light that is directly backscattered from the target focal volume to be detected by the sensor. Light that reaches the sensor, but is returned from outside the target focal volume, or reflected from components within the imaging system, is reduced in intensity or eliminated from the image.

In accordance with another embodiment of the present invention, the illumination source and spatial light modulator produce a series of lines parallel to the rolling shutter in rapid succession across the field of view of the target, and the timing of the illumination pattern is matched to that of the rolling shutter at a conjugate image plane. In this embodiment, the target is imaged in transmission mode (i.e., light passes through the target), with the sensor positioned to collect forward scattered light from the target. Light that reaches the sensor, but is returned from outside the target focal volume, is reduced in intensity or eliminated from the image.

In accordance with yet another embodiment of the present invention, the illumination source and spatial light modulator produce a series of lines parallel to the rolling shutter in rapid succession across the field of view of the target, and the timing of the illumination pattern with respect to the rolling shutter at a conjugate image plane is set to a known offset. In this embodiment, the rolling shutter confocal aperture detects multiply scattered light from the target, performing so-called dark-field imaging. In a related embodiment, the sensor and spatial light modulator frame rates are offset in frequency to provide a series of frame exposures with varied timing offsets that repeat according to a beat frequency. In this embodiment, the timing signal synchronizes the start of the exposure and illumination frames at least once per beat period. The frames are post-processed to enhance image contrast or determine scattering properties of the target.

In still another illustrative embodiment of the present invention, the illumination source and spatial light modulator produce a series of lines parallel to the rolling shutter in rapid succession across the field of view of the target, and the timing of the illumination pattern is matched to that of the rolling shutter at a conjugate image plane. The geometry of the illumination pattern within the width of the rolling shutter is varied from one frame to the next. A series of frames are acquired and processed to modify the spatial filtering transfer function of the confocal imaging device.

In accordance with yet another embodiment, the illumination source and spatial light modulator produce a series of lines parallel to the rolling shutter in rapid succession across the field of view, and the timing of the illumination pattern is matched to that of the rolling shutter at a conjugate image plane. The width of the illumination lines is varied from one frame to the next. A series of frames are acquired and processed to determine scattering properties of the target.

In accordance with another embodiment, the illumination source and spatial light modulator produce a series of lines parallel to the rolling shutter in rapid succession across the field of view of the target. The width of the confocal rolling shutter is varied from one frame to the next. A series of frames are acquired and processed to determine properties of light returning from the target or to modify the spatial filtering transfer function of the confocal imaging device. In a related embodiment, the confocal rolling shutter width is varied together with one or more of: a timing offset between the rolling shutter and illumination pattern, or a change in the shape of the illumination pattern. A series of frames are acquired and processed to determine properties of light returning from the target or to modify the spatial filtering transfer function of the confocal imaging device.

In another illustrative embodiment, the illumination source and spatial light modulator produce a series of lines parallel to the rolling shutter in rapid succession across the field of view of a target. Acquired image frames are post-processed to provide real-time adjustments to the shape of the illumination pattern to compensate for lens aberrations in the imaging system. A means of control may apply any of variable illumination line widths, illumination line curvature, and variable speeds of line progression across the field of view to achieve better timing synchronization and confocal image quality.

In still another illustrative embodiment, the illumination source and spatial light modulator are integrated in a digital light projector, which is driven using a video card from a personal computer, laptop, tablet, single-board computer, mobile device, or other display generator. In this embodiment, the video card or display generator provides the timing signal to coordinate the illumination pattern with the rolling shutter position. The timing signal from the video card or generator is processed so that it can drive the sensor's external trigger and create a substantially controlled timing relationship between a video and a sensor exposure frame. Related embodiments to establish timing synchronization and frame-to-frame image stability include the use of: the strobe output signal from a spatial light modulator, the strobe output signal from the sensor, a trigger signal used to drive the spatial light modulator, or a master clock signal derived from a separate timing source.

In accordance with another embodiment, the spatial light modulator operates at a faster frame rate than the sensor. This embodiment permits changes to the illumination pattern during each exposure frame of the sensor, such as the illumination wavelength, illumination intensity, pattern shape, and pattern timing. Such intra-frame modifications may be preset by the operator and in response to images previously acquired by the sensor. Such intra-frame modifications may be performed to reduce the amount of light exposure to specific regions of the target to avoid damage or photobleaching, or to adjust the variation in the amount of light returned across the field of view of the target.

In accordance with another embodiment, the illumination pattern is provided by a digital light projector that is operated in a structured illumination output mode. An example of one such mode converts a wide range of values for color or grayscale at a lower speed to a more limited number of values at a more rapid output, such as an 8-bit RGB channel at 60 Hz to a 1-bit monochrome output at 1440 Hz, which can permit a narrower instantaneous line on the target for a given sensor frame rate, depending on the resolution of the micromirror array, field size, and magnification of the imaging system. Other structured light illumination output modes include the use of preset illumination patterns, or illumination patterns loaded into the memory of the digital light projector, in order to increase the illumination frame rate.

In yet another embodiment, the spatial light modulator operates at a faster frame rate than the sensor. In this embodiment, the illumination source and spatial light modulator are integrated in a digital light projector capable of operating in a structured illumination mode. During each video input frame, the digital light projector is configured to project a series of lines parallel to the rolling shutter in rapid succession. The range of illumination lines produced by each video frame is decreased to cover only a subset of the field of view. In this embodiment, the illumination range can be smaller than the field of view by up to the ratio of the video to sensor frame rate. A narrower illumination range can permit a narrower instantaneous line on the target, depending on the resolution of the micromirror array, field size, magnification, and frame rate of the imaging system and spatial light modulator. In this embodiment, the timing signal matches the position of the rolling shutter with the conjugate modulation pattern, and can be derived from one or more video frames during each sensor frame. In a related embodiment, the subset range of illumination provided by each video frame used to drive the digital light projector is duplicated and projected simultaneously across the field of view. Provided the illumination range is sufficiently larger than the confocal rolling shutter width, light return from the undesired illumination ranges will be spatially filtered and will minimally contribute to the acquired image.

In accordance with one embodiment, the illumination source and spatial light modulator produce a series of lines parallel to the rolling shutter in rapid succession across the field of view of the target. The light returned from the target is spatially separated according to its polarization using an anisotropic material placed in the detection pathway, which is defined as the optical path between the target and sensor. In this embodiment, the spatial separation of the polarization of light returned from the target is produced substantially perpendicular to the rolling shutter so that the spatial filtering provided by the rolling shutter acts as a polarizing filter. By varying the timing offset between the illumination pattern and rolling shutter, the sensor can selectively detect light from horizontal and vertical polarizations. In a related embodiment, a polarizing beamsplitter is inserted in the detection pathway, which is defined as the optical path between the target and sensor. A second pixel array detector having rolling shutter functionality is inserted so that horizontal and vertical polarized light return from the target may be independently detected simultaneously. In this embodiment, an anisotropic material is no longer necessary. In another related embodiment, a polarizer and waveplate are inserted into the illumination pathway, which is defined as the optical path between the illumination source and target, to perform polarization sensitive imaging. In this embodiment, a series of frames that measure horizontal and vertical polarization are acquired at varied illumination polarization states. The frames are post-processed to determine birefringence, diattenuation, and scattering properties of the target.

According to yet another illustrative embodiment, the illumination source and spatial light modulator produce a series of lines parallel to the rolling shutter in rapid succession across the field of view of the target. The light returned from the target is spatially separated according to its frequency using a dispersive grating or prism placed in the detection pathway, defined as the optical path between the target and sensor. In this embodiment, the spatial separation of the frequency of scattered light is produced substantially perpendicular to the rolling shutter so that the spatial filtering provided by the rolling shutter acts as a bandpass filter. By varying the timing offset between the illumination pattern and rolling shutter, the center frequency of the bandpass filter can be adjusted. By varying the rolling shutter width, optical magnification, or the amount of dispersion added to the detection pathway, the width of the frequency filter can be adjusted. By varying the illumination pattern shape, the filter transfer function can be adjusted in both center frequency and bandwidth. In this embodiment, a series of frames can be acquired with varied timing offsets or illumination pattern shapes to perform spectroscopy or multi-wavelength imaging. In a related embodiment, the dispersive element is configured to detect light returning from the target that is not at the same frequency as the light used for illumination. In this embodiment, an optical filter may be added to the detection pathway to prevent light at the illumination frequency from being detected. In another related embodiment, multiple sources are used to provide illumination at various wavelengths to provide greater spectroscopic characterization of the target. In yet another related embodiment, a portion of the light return from the target is directed to a dispersive element and pixel array detector. The remaining light return from the target is directed to a second pixel array detector to simultaneously perform confocal imaging of the target.

In still another illustrative embodiment, the system is configured for spectral domain optical coherence tomography (SD-OCT). In this embodiment, a Michelson interferometer is used to direct a portion of the light travelling from the spatial light modulator toward the target through a reference path of known optical length. The light directed through the reference path is combined with the light returned from the target and is spatially separated according to its frequency using a dispersive grating or prism placed in the detection pathway. In this embodiment, the light is dispersed substantially along the length of the rolling shutter. The illumination source and spatial light modulator produce a series of points in rapid succession across the field of view of the target. The timing of the illumination pattern is matched to that of the rolling shutter at a conjugate image plane. This embodiment uses the rolling shutter confocal aperture to measure the interferometric spectrum of the light that is directly backscattered from the target focal volume. Each sensor frame collects what is commonly referred to as an OCT B-scan. After each frame, the illumination pattern can be adjusted to perform a B-scan at another target location and thereby construct a 3-dimensional SD-OCT image. In a related embodiment, multiple OCT B-scans are recorded simultaneously by illuminating multiple target regions parallel to the rolling shutter at the same time. In this embodiment, the illumination points are sufficiently separated in the field of view that cross-talk effects are sufficiently small to permit OCT imaging. In a related embodiment, overlapping spectral interferograms from multiple simultaneous OCT B-scans are deconvolved in post-processing. In another related embodiment, the target is illuminated using multiple illumination sources with different power spectra. The sources may illuminate the same region of the target at substantially the same time in order to modify the detected spectrum of the interferogram and, by extension, the OCT point-spread function and depth resolution. The sources may illuminate different regions of the target at substantially the same time in order to perform multiple B-scans simultaneously.

According to another illustrative embodiment, the SD-OCT optical design is supplemented by adding an anisotropic material to the detection pathway to spatially separate the light according to its polarization in a direction perpendicular to the rolling shutter. By varying the timing offset between the illumination pattern and rolling shutter, the interferometric spectrum of light is selectively measured at either horizontal or vertical polarizations. When a wave plate is added to the reference arm, one polarization component can be delayed by a quarter-wave with respect to the other, allowing quadrature detection of the interferometric signal. Quadrature detection may be used to resolve the complex OCT signal and yield full depth range axial scans. In a related embodiment, a polarizer and waveplate are inserted into the illumination pathway to perform polarization-sensitive SD-OCT.

In one illustrative embodiment, the placement of the target, sensor and spatial light modulator is configured for Fourier-plane imaging. In this embodiment, the sensor is conjugate to the spatial light modulator and the illumination source, which produce a series of lines parallel to the rolling shutter in rapid succession. The target is placed at a Fourier plane with respect to the sensor and spatial light modulator. The target may be translated or rotated through the illumination focal volume.

The spatial filtering provided by the rolling shutter serves to select the angle of light scattered from the target. In this embodiment, the use of a spatially coherent illumination source with sufficient spatial filtering can substantially provide detection of plane waves scattered from the target. By varying the timing offset between the illumination pattern and rolling shutter, the detected scattering angle for a given angle of illumination can be measured, providing a scattering or diffractive characterization of the target. In a related embodiment, an image of the target is reconstructed from the diffraction pattern detected by the sensor. In a related embodiment, the illumination source and spatial light modulator produce multiple lines parallel to the rolling shutter in rapid succession. Each line illuminates the target from a different angle, which can be different from the angle of light return that is detected using the rolling shutter. In another related embodiment, the illumination source and spatial light modulator produce multiple lines, each at a different illumination center wavelength, parallel to the rolling shutter in rapid succession. A color CMOS sensor with rolling shutter functionality is used to detect an angle of light return from the target for each of the illumination angles. In this embodiment, the illumination spectra substantially overlap with the filter response functions for the color CMOS sensor pixels. The detection of a specified angle of light returning from the target in response to one or more specified illumination angles allows a user to perform differential interference contrast imaging, digital holography, synthetic aperture imaging, and phase-contrast imaging.

In still another embodiment, the Fourier plane optical design is supplemented by adding a Michelson or Mach-Zehnder interferometer to combine light from a reference pathway with angularly filtered light returned from the target. A dove prism may be added to the reference pathway to invert the angle of light with respect to the illumination angle. By varying the timing offset between the illumination pattern and rolling shutter, different spatial frequencies of the interference between the backscattered and reference light may be measured. Light is collected at a variety of angular scattering and illumination geometries to perform interferometry, digital holography, synthetic aperture imaging, and phase-contrast imaging. In a related embodiment, the Fourier-plane optical design is adapted for synthetic aperture ophthalmic imaging. This embodiment may be used to generate images at higher resolution than normally attainable with the numerical aperture limited by the anatomy of the living eye.

According to yet another illustrative embodiment, the Fourier-plane optical design is supplemented by adding a reference pathway and dispersive element to perform SD-OCT. In this embodiment, the angular selectivity of the scattered light provided by the rolling shutter permits the acquisition of a series of angular B-scans, which can be used to reconstruct a high-contrast 3-dimensional image using techniques common in computed tomography imaging. The angular selectivity of the light returning from the target provided by the rolling shutter further provides characterization of the scattering properties of the target. By monitoring scattering changes over time, this embodiment may be used to measure the velocity of moving portions of the target.

In accordance with still another illustrative embodiment, the placement of the target, sensor and spatial light modulator is configured for Fourier-plane imaging. In this embodiment, the target is conjugate to the spatial light modulator and the spatial light modulator produces a series of lines parallel to the rolling shutter in rapid succession. The sensor is placed near the Fourier plane, such that the rolling shutter detects a series of collimated lines synchronized to the output of the spatial light modulator. In this configuration, the rolling shutter is set to predominantly detect the Fourier transform of the light scattered from the illumination focal volume. In a related embodiment, the optical design is supplemented by adding a Michelson or Mach-Zehnder interferometer to combine light from a reference pathway to the light backscattered from the target. In this embodiment, the reference arm light is incident on the sensor at an angle with respect to the light backscattered from the target to perform digital holography.

According to one illustrative embodiment, the optical design is supplemented by adding one or more lenses for the purpose of imaging a human or animal retina. In this ophthalmic imaging embodiment, the spatial light modulator produces a series of lines parallel to the rolling shutter in rapid succession across the field of view of the retina. The sensor is placed in a plane conjugate to the retina. In this embodiment, the Fourier plane is also called a pupil plane and is made conjugate to the pupil of the subject being imaged. A fixed aperture is placed at a conjugate pupil plane between the spatial light modulator and target to limit the illumination to a specific portion of the pupil. The light scattered from the retina is also spatially filtered with an aperture placed in a conjugate pupil plane between the eye and the sensor. The spatial filtering at the conjugate pupil plane serves to separate the illumination light from the imaging light and thereby reduce unwanted reflections and scattering from the anterior segment of the eye. To those skilled in the art, this method of separating the illumination pupil from the imaging pupil is known as the Gullstrand Principle. In this embodiment, the geometry of the illumination and imaging pupils can take on any shape set by the apertures. Aperture geometries commonly used in the art to separate the illumination from the imaging pupil include: circular geometries, annulus or ring-shaped geometries, and pupil geometries with side-to-side separation. In related embodiments, the shape and timing offset of the rolling shutter and illumination pattern provided by the spatial light modulator may be altered to perform dark-field imaging in the eye. Multiple frames may also be acquired and post-processed to enhance image contrast or determine scattering properties of the target, as discussed previously. Other embodiments include the use of a dispersive element to perform spectroscopy or fluorescence imaging, or an anisotropic element to perform polarimetry, in the eye. Yet another embodiment includes the use of a Michelson interferometer with a reference pathway and a dispersive grating to perform SD-OCT imaging of the retina. In this embodiment, the imaging light may be sent to two sensors with rolling shutters for simultaneous SD-OCT and standard confocal imaging. Registration of the standard confocal images may be used to compensate for the motion of the eye during the acquisition of a 3-dimensional SD-OCT image set.

In accordance with another illustrative embodiment, multiple sources are used to illuminate the spatial light modulator and target at various wavelengths to enhance the image contrast or visibility, depending on the target's light remitting characteristics. In this embodiment, the spatial light modulator and illumination sources may be integrated into a digital light projector with separate red, green and blue channels. In a related embodiment, one or more illumination source built into the digital light projector may be swapped with an external light source with more desirable power, polarization, coherence, longitudinal or transverse operating mode, or frequency characteristics for the target being imaged. In this embodiment, the operating parameters of the illumination sources, such as the driving current, frequency, phase, pulse width, and duty cycle may be pre-set by the operator, or adjusted in response to acquired image data. In a related embodiment adapted for ophthalmic imaging, one or more illumination source is used for imaging, while at least one other is used to direct the gaze of the subject, or to stimulate a portion of the retina for visual function testing. Registration of the standard confocal images may be used to compensate for the motion of the eye during visual function testing.

In accordance with one illustrative embodiment, a second spatial light modulator is used in conjunction with the first to control the amplitude and phase of the light reaching the target. In this embodiment, the first spatial light modulator is a digital micromirror array and the second is an array of liquid crystal elements. The liquid crystal array is placed in a Fourier plane with respect to the micromirror array. The light from the illumination source is polarized according to the axis of induced birefringence in the liquid crystal array. The illumination source is directed onto the micromirror array, which creates an illumination modulation pattern that is directed through the liquid crystal array before reaching the target. The liquid crystal elements share the same timing relationship as the micromirror array and rolling shutter. By adjusting the induced birefringence applied to the liquid crystal pixels, the illumination light undergoes a phase delay, altering the wavefront of the illumination beam. In this embodiment, images may be used as feedback to adjust the phase delay, or a user may specify a desired phase delay. By adjusting the wavefront of the illumination beam in conjunction with the illumination pattern provided by the micromirror array, the spot size or line width at the target may be optimized across the field of view according to the target shape, distance from the device, focus, or aberrations caused by optical components within the device. In a related embodiment, a spatial light modulator is added to a Fourier plane in the detection pathway, which is defined as the light path taken from the target to the detector. The spatial light modulator may be used to adjust the wavefront of the light backscattered from the target to optimize the spot size or line width across the field of view at the sensor. The spatial light modulator may also be used to induce phase steps to the light backscattered from the target to perform diffraction tomography.

In one embodiment of the present invention, the illumination source and spatial light modulator produce a series of lines parallel to the rolling shutter in rapid succession across the field of view of the target. The timing of the illumination pattern is matched to that of the rolling shutter at a conjugate image plane. In this embodiment, a wavefront controller, such as a deformable mirror, is placed in a Fourier plane with respect to the spatial light modulator, target, and sensor, and that is located in the detection pathway, which is defined as the optical path between the target and sensor. By adjusting the wavefront controller, the wavefront of the imaging light is modified to correct aberrations caused by the imaging system or to adjust the focus and thereby improve feature contrast and image quality. In a related embodiment, a beamsplitter is added to the detection pathway to direct a portion of the light returning from the target to a wavefront detector, such as a Shack-Hartman wavefront sensor. The wavefront detector measures a portion of the light return from the target to provide feedback to the wavefront controller. In a related embodiment, image data is processed and used as feedback to modify the wavefront using the wavefront controller. In a related embodiment, a user specifies a desired wavefront in software that is applied to the wavefront controller, with image data or a wavefront detector providing feedback to the wavefront controller.

BRIEF DESCRIPTION OF THE DRAWINGS

The above-mentioned aspects of the present invention and the manner of obtaining them will become more apparent and the invention itself will be better understood by reference to the following description of the embodiments of the invention taken in conjunction with the accompanying drawings, wherein:

FIG. 13 depicts an intra-frame rolling shutter and multiple strip illumination position for confocal imaging in accordance with teachings of the present invention.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Figure 1:
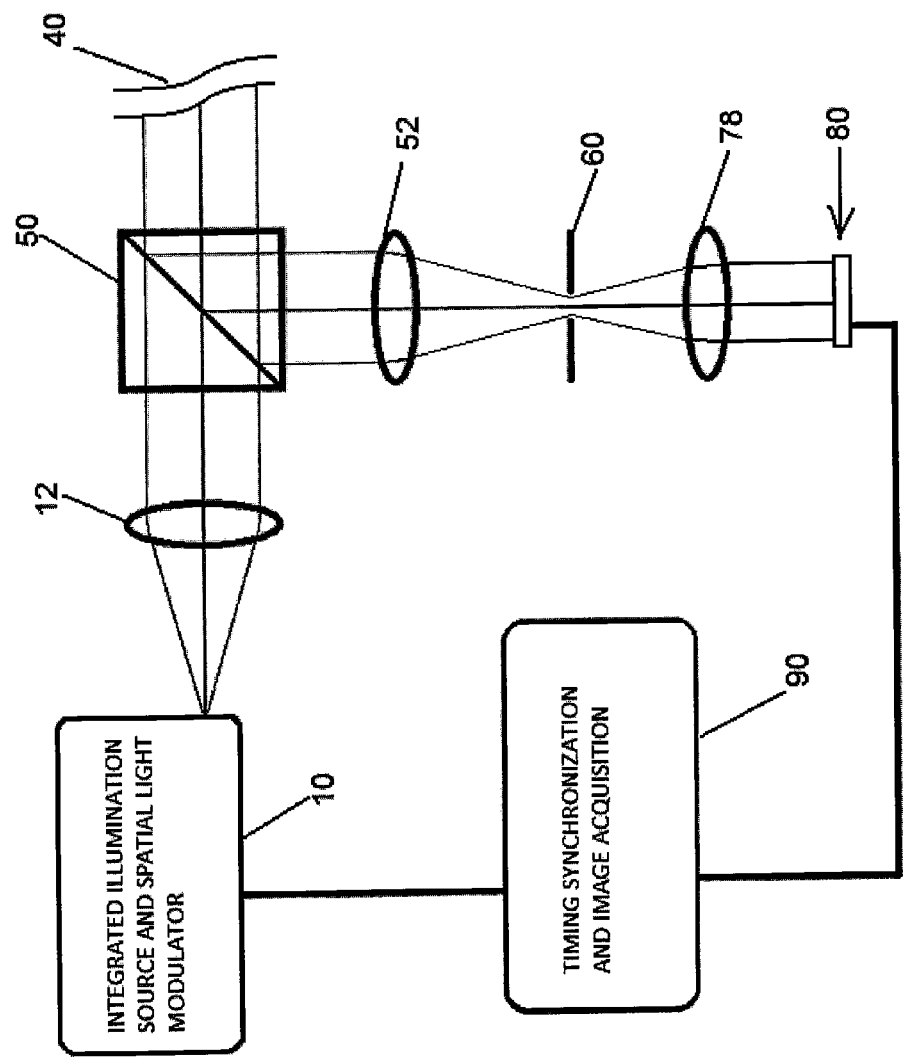
FIG. 1 is a schematic diagram of a confocal imaging device with simulated line scanning in accordance with the teachings of the present invention.

FIG. 1 shows one embodiment of the present invention for performing confocal imaging of a target. In accordance with this embodiment, an integrated spatial light modulator and illumination source 10 produce a series of lines parallel to a rolling shutter on a two-dimensional (2D) pixel array sensor 80. The lines are projected in rapid succession across the field of view of the target 40 to simulate line-scanning. In this illustrative embodiment, the integrated spatial light modulator and illumination source 10 is a compact and lightweight digital light projector (DLP), which can be handheld. A lens 12 is used to collimate the DLP output and set the focal plane of the target 40 to be conjugate to the micromirror array used in the DLP. A beamsplitter 50 directs a portion of the backscattered light from the target 40 toward the sensor 80. An optical relay system, including lenses 52 and 78, adjusts the magnification between the target 40 and sensor 80 so that the illumination field of view approximately matches the active pixel region of interest on the sensor 80. The optical relay system also serves to set the focal plane of the sensor 80 to be conjugate to the target 40, and the micromirror array of the DLP illumination source 10. An aperture stop 60 is optionally placed in the Fourier plane of the sensor 80 to reduce unwanted scattering, reflections, or light from the surrounding environment from reaching the sensor 80. In accordance with certain aspects of this embodiment, a video output signal driving the DLP illumination source 10 is filtered and used to externally trigger the sensor 80 to establish a substantially fixed spatial-temporal relationship between an illumination stripe and rolling shutter 90. Adjustments to any of the sensor's trigger delay, starting row or column, shutter width, or to the DLP stripe position and width allow precise software-based spatial-temporal alignment between the illumination stripe and rolling shutter position. It should be understood and appreciated by those of skill in the art that these attributes may be adjusted by a variety of control methods in real-time to perform calibration, or a variety of other embodiments, as described herein. As such, the present teachings are not intended to be limiting herein.

Figure 2:
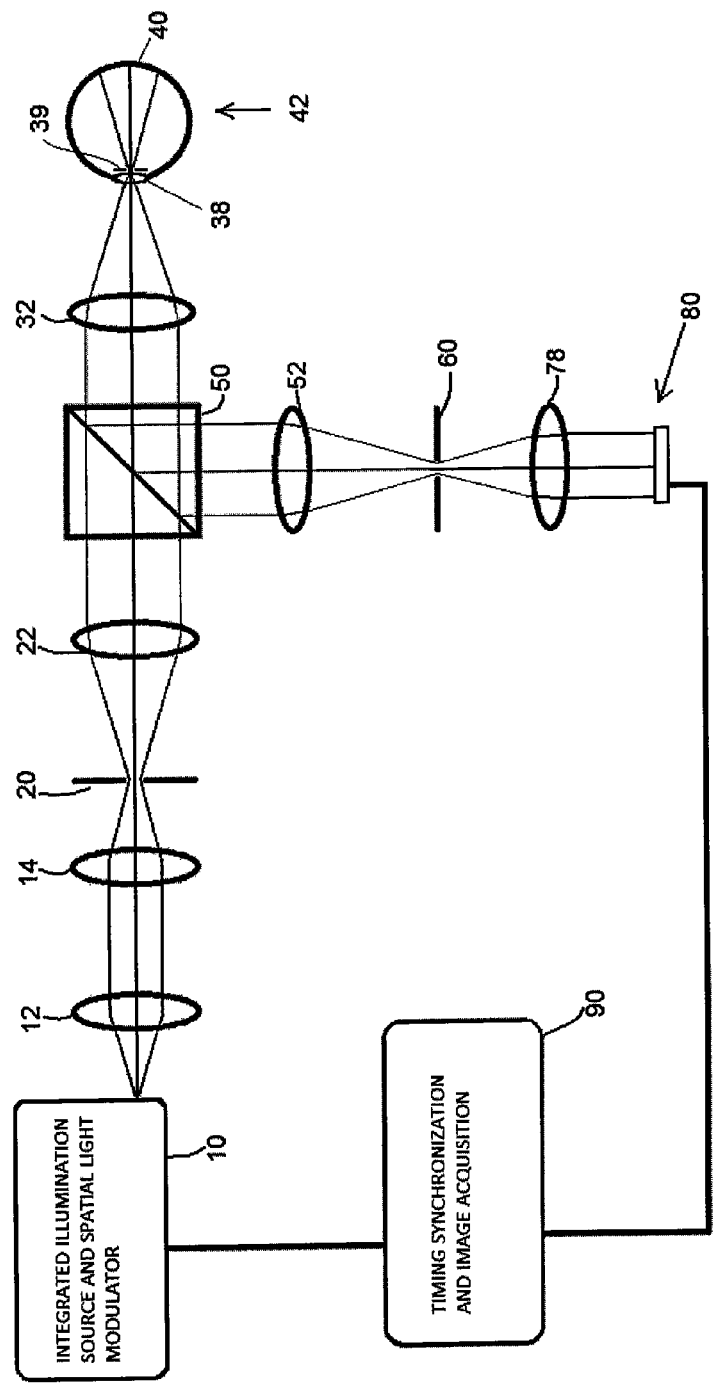
FIG. 2 is a schematic diagram of a confocal ophthalmoscope with simulated line scanning in accordance with the teachings of the present invention.

FIG. 2 depicts an illustrative embodiment for performing confocal imaging of a living eye 42 in accordance with the teachings of the present invention. Here, the integrated spatial light modulator and illumination source 10 produce a series of lines parallel to the rolling shutter on a 2-dimensional pixel array sensor 80. The illumination is directed through the lens 38 and pupil 39 of the eye 42 and focused to a series of lines projected in rapid succession across the field of view of the retina target 40 to simulate line-scanning. In accordance with certain aspects of this embodiment, the integrated spatial light modulator and illumination source 10 is a compact and lightweight digital light projector (DLP), which can be handheld. An optical relay system, including lenses 12, 14 and 22, adjusts the magnification of the Fourier plane (also referred to as "the pupil plane" in accordance with this illustrative embodiment). An aperture stop 20 is placed in the pupil plane to set an entrance pupil geometry. The exit pupil geometry is set by aperture stop 60 in a conjugate pupil plane. Aperture stops 20 and 60 are used together to spatially separate the light that enters the pupil 39 from light that exits the pupil 39 for the purpose of reducing unwanted scattering and reflections from lenses and the anterior segment of the eye. The distance between lenses 22 and 32 is adjusted to set the focal plane of the retina 40 to be conjugate to the micromirror array of the DLP illumination source 10. In accordance with certain aspects of this embodiment, the distance between lenses 22 and 32 is adjusted while maintaining a constant distance between lenses 22 and 52 so that the sensor 80 is at a plane conjugate to the micromirror array of the DLP illumination source 10 regardless of the optical length of the eye. A beamsplitter 50 directs a portion of the light return from the retina target 40 toward the sensor 80. An optical relay system, including lenses 52 and 78, adjusts the magnification between the retina target 40 and sensor 80 so that the illumination field of view approximately matches the active pixel region of interest on the sensor 80. The optical relay system also serves to set the focal plane of the sensor 80 to be conjugate to the micromirror array of the DLP illumination source 10. In accordance with certain aspects of this illustrative embodiment, a video output signal driving the DLP illumination source 10 is filtered and used to externally trigger the sensor 80 to establish a substantially fixed spatial-temporal relationship between the illumination stripe and rolling shutter 90. Adjustments to any of the sensor's trigger delay, starting row or column, shutter width, or to the DLP stripe position and width allow precise software-based spatial-temporal alignment between the illumination stripe and rolling shutter position. It should be understood and appreciated by those of skill in the art that these attributes may be adjusted by a variety of control methods in real-time to perform calibration, or a variety of other embodiments, as described herein.

Figure 3:
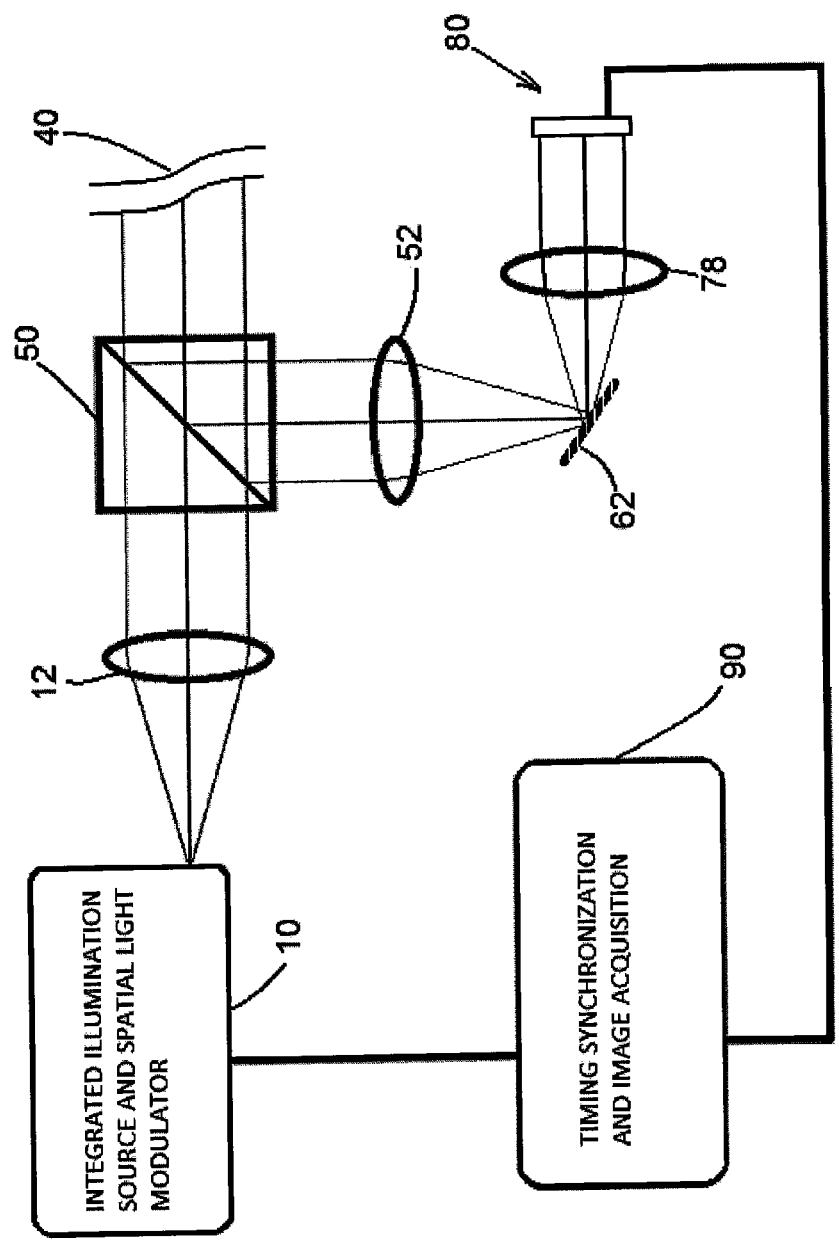
FIG. 3 is a schematic diagram of a confocal spectral imaging device with simulated line scanning in accordance with the teachings of the present invention.

FIG. 3 depicts an illustrative embodiment in accordance with certain aspects of the present invention in which confocal, spectrally filtered, imaging of a target is performed. In accordance with this embodiment, the integrated spatial light modulator and illumination source 10 produces a series of lines parallel to the rolling shutter on a 2-dimensional pixel array sensor 80. The lines are projected in rapid succession across the field of view of the target 40 to simulate line-scanning. In accordance with certain aspects of this embodiment, the integrated spatial light modulator and illumination source 10 is a lightweight and compact digital light projector (DLP), which can be handheld. A lens 12 is used to collimate the DLP output and set the target focal plane 40 to be conjugate to the micromirror array used in the DLP. A beamsplitter 50 directs a portion of the light return from the target 40 toward the sensor 80. An optical relay system, including lenses 52 and 78 adjusts the magnification between the target 40 and the sensor 80 so that the illumination field of view approximately matches the active pixel region of interest on the sensor 80. The optical relay system also serves to set the focal plane of the sensor 80 to be conjugate to the target 40, and the micromirror array of the DLP illumination source 10. A dispersive element, such as a grating 62, is placed in the Fourier plane of the sensor 80 to disperse the spectral content of the light returning from the target 40. The dispersive element 62 is aligned so that dispersion occurs substantially perpendicular to the rolling shutter. In accordance with this illustrative embodiment, a video output signal driving the DLP illumination source 10 is filtered and used to externally trigger the sensor 80 to establish a substantially fixed spatial-temporal relationship between an illumination stripe and rolling shutter 90. Adjustments to any of the sensor's trigger delay, starting row or column, shutter width, or to the DLP stripe position and width allow precise software-based spatial-temporal alignment between the illumination stripe and rolling shutter position. It should be understood and appreciated by those of skill in the art that these attributes may be adjusted by a variety of control methods in real-time to perform calibration, or a variety of other embodiments, as described herein.

Figure 4:
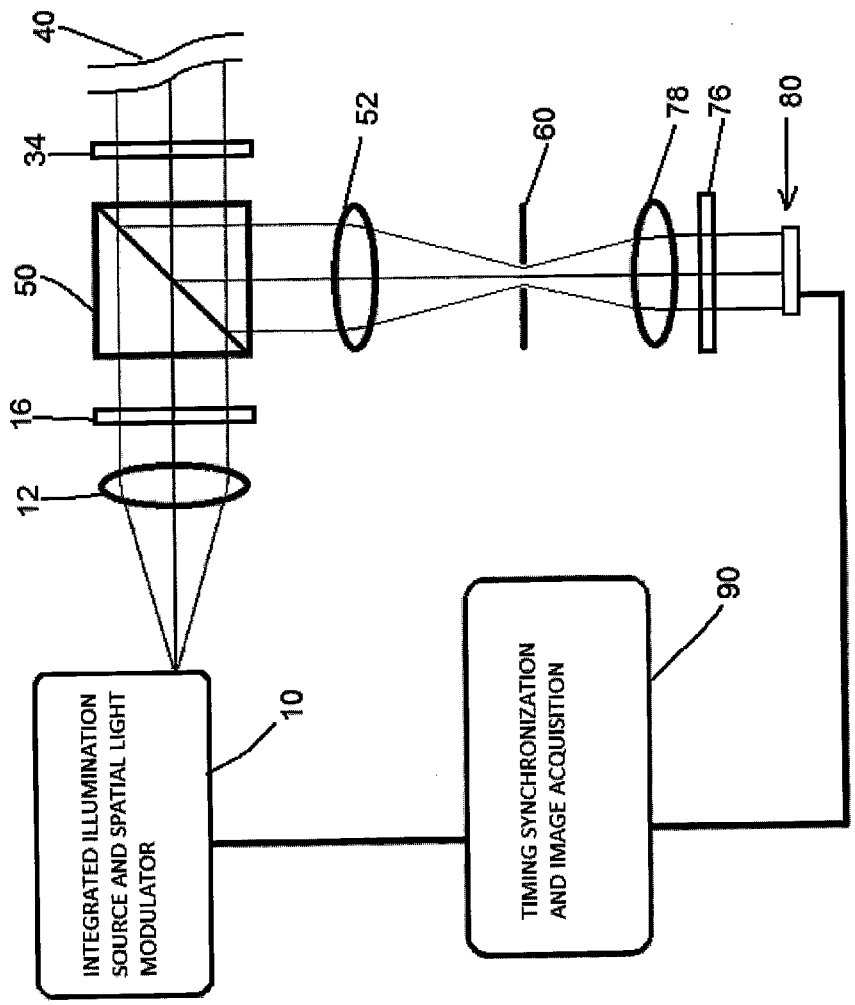
FIG. 4 is a schematic diagram of a confocal polarization sensitive imaging device with simulated line scanning in accordance with the teachings of the present invention.

FIG. 4 is directed to another illustrative embodiment for performing confocal, polarization sensitive, imaging of a target in accordance with certain aspects of the present invention. In accordance with this illustrative embodiment, the integrated spatial light modulator and illumination source 10 produces a series of lines parallel to the rolling shutter on a 2-dimensional pixel array sensor 80. The lines are projected in rapid succession across the field of view of the target 40 to simulate line-scanning. In accordance with certain aspects of this embodiment, the integrated spatial light modulator and illumination source 10 is a compact and lightweight digital light projector (DLP), which can be handheld. A lens 12 is used to collimate the DLP output and set the focal plane of the target 40 to be conjugate to the micromirror array used in the DLP. A polarizer 16 filters the illumination so that it is linearly polarized, and a birefringent material, such as a quarter-wave plate, 34 is set to rotate the polarization of the illumination light and the light return from the target 40 by a quarter wave. A beamsplitter 50 directs a portion of the light return from the target 40 toward the sensor 80. An optical relay system, including lenses 52 and 78, adjusts the magnification between the target 40 and sensor 80 so that the illumination field of view approximately matches the active pixel region of interest on the sensor 80. The optical relay system also serves to set the focal plane of the sensor 80 to be conjugate to the target 40, and the micromirror array of the DLP illumination system 10. An aperture stop 60 is optionally placed in the Fourier plane of the sensor 80 to reduce unwanted scattering, reflections, or light from the surrounding environment from reaching the sensor 80. A birefringent beam displacing element 76 spatially separates the light return from the target according to its polarization. In this embodiment, the beam is displaced in a direction perpendicular to the rolling shutter so that the polarization components of the light return from the target can be imaged independently by adjusting the timing offset between the rolling shutter and illumination pattern. The polarizer 16 may be rotated from one frame to the next to adjust the illumination polarization. In accordance with certain aspects of this illustrative embodiment, a video output signal driving the DLP illumination source 10 is filtered and used to externally trigger the sensor 80 to establish a substantially fixed spatial-temporal relationship between the illumination stripe and rolling shutter 90. Adjustments to any of the sensor's trigger delay, starting row or column, shutter width, or to the DLP stripe position and width allow precise software-based spatial-temporal alignment between the illumination stripe and rolling shutter position. It should be understood and appreciated by those of skill in the art that these attributes may be adjusted by a variety of control methods in real-time to perform calibration, or a variety of other embodiments, as described herein.

Figure 5:
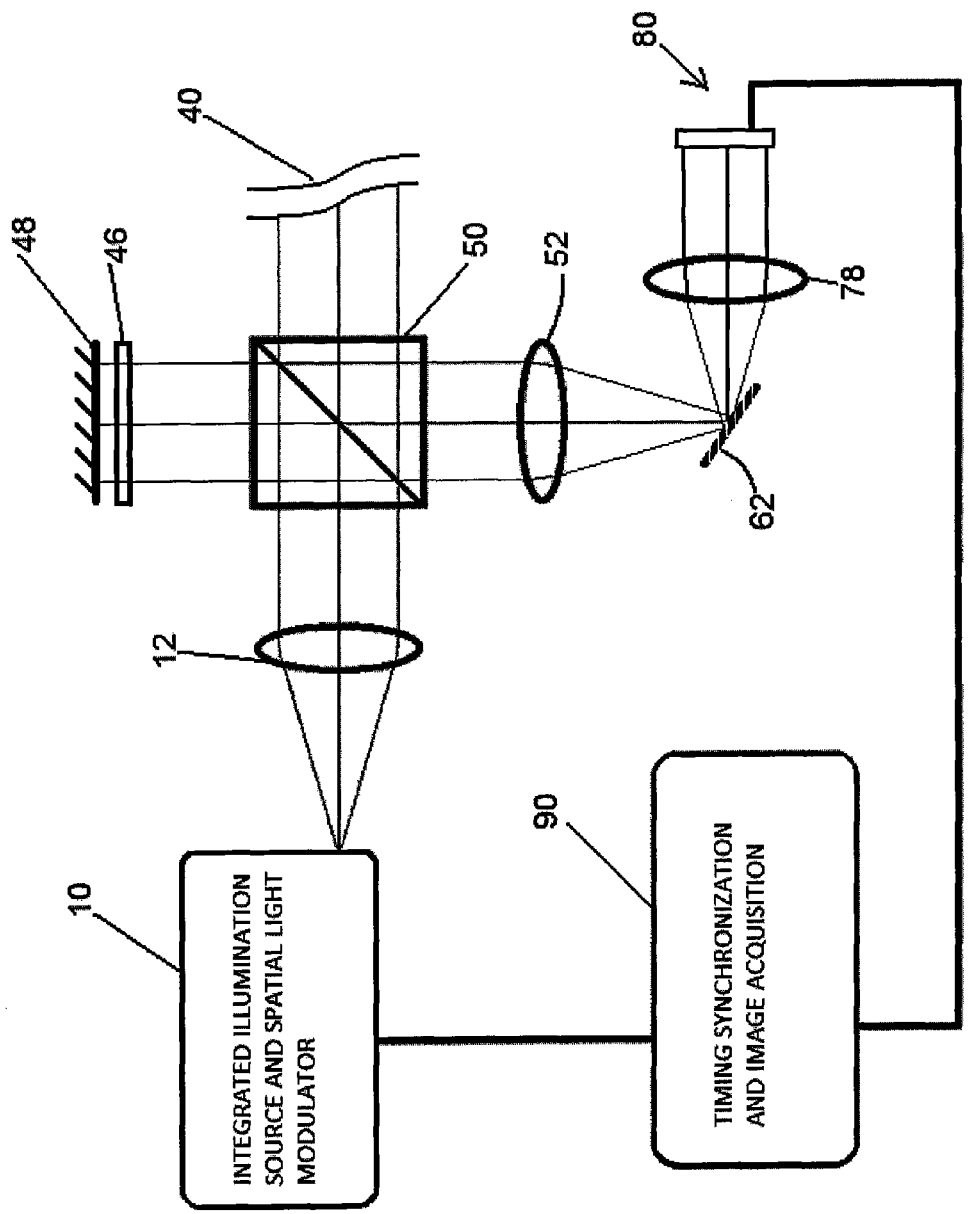
FIG. 5 is a schematic diagram of a spectral domain optical coherence tomography imaging device with simulated point scanning in accordance with the teachings of the present invention.

Moving now to FIG. 5, an illustrative embodiment for performing confocal, spectral-domain optical coherence tomography (SD-OCT) imaging of a target in accordance with certain aspects of the present invention is shown. The integrated spatial light modulator and illumination source 10 produces a series of points in rapid succession across the field of view of the target 40 to simulate point-scanning. The fast-axis of the simulated point-scanning is substantially aligned perpendicular to the rolling shutter on a 2-dimensional pixel array sensor 80. In accordance to this illustrative embodiment, the integrated spatial light modulator and illumination source 10 is a compact and lightweight digital light projector (DLP), which can be handheld. A lens 12 is used to collimate the DLP output and set the focal plane of the target 40 to be conjugate to the micromirror array used in the DLP. A beamsplitter 50 is used to create a Michelson interferometer, whereby a portion of the illumination light is directed to the target 40 and to a reference pathway with known optical path delay. An optical attenuator, such as a neutral density filter, 46 adjusts the reference arm intensity, and a mirror 48 sends the light back to the beamsplitter 50, which combines a portion of the light returning from the target 40 with a portion of light reflected from the reference arm mirror 48 and directs it toward the sensor 80. An optical relay system, including lenses 52 and 78, adjusts the magnification between the target 40 and sensor 80 so that the illumination field of view approximately matches the active pixel region of interest on the sensor 80. The optical relay system also serves to set the focal plane of the sensor 80 to be conjugate to the target 40, and the micromirror array of the DLP illumination source 10. A dispersive element, such as a grating, 62 is placed in the Fourier plane of the sensor 80 to disperse the spectral content of the combined light return from the target 40 and from the reference arm. The dispersive element 62 is aligned so that dispersion occurs substantially parallel to the rolling shutter, allowing the spectral interferogram to be measured at each illumination point. In accordance with certain aspects of this illustrative embodiment, a video output signal driving the DLP illumination source 10 is filtered and used to externally trigger the sensor 80 to establish a substantially fixed spatial-temporal relationship between the illumination stripe and rolling shutter 90. Adjustments to any of the sensor's trigger delay, starting row or column, shutter width, or to the DLP stripe position and width allow precise software-based spatial-temporal alignment between the illumination stripe and rolling shutter position. It should be understood and appreciated by those of skill in the art that these attributes may be adjusted by a variety of control methods in real-time to perform calibration, or a variety of other embodiments, as described herein.

Figure 6:
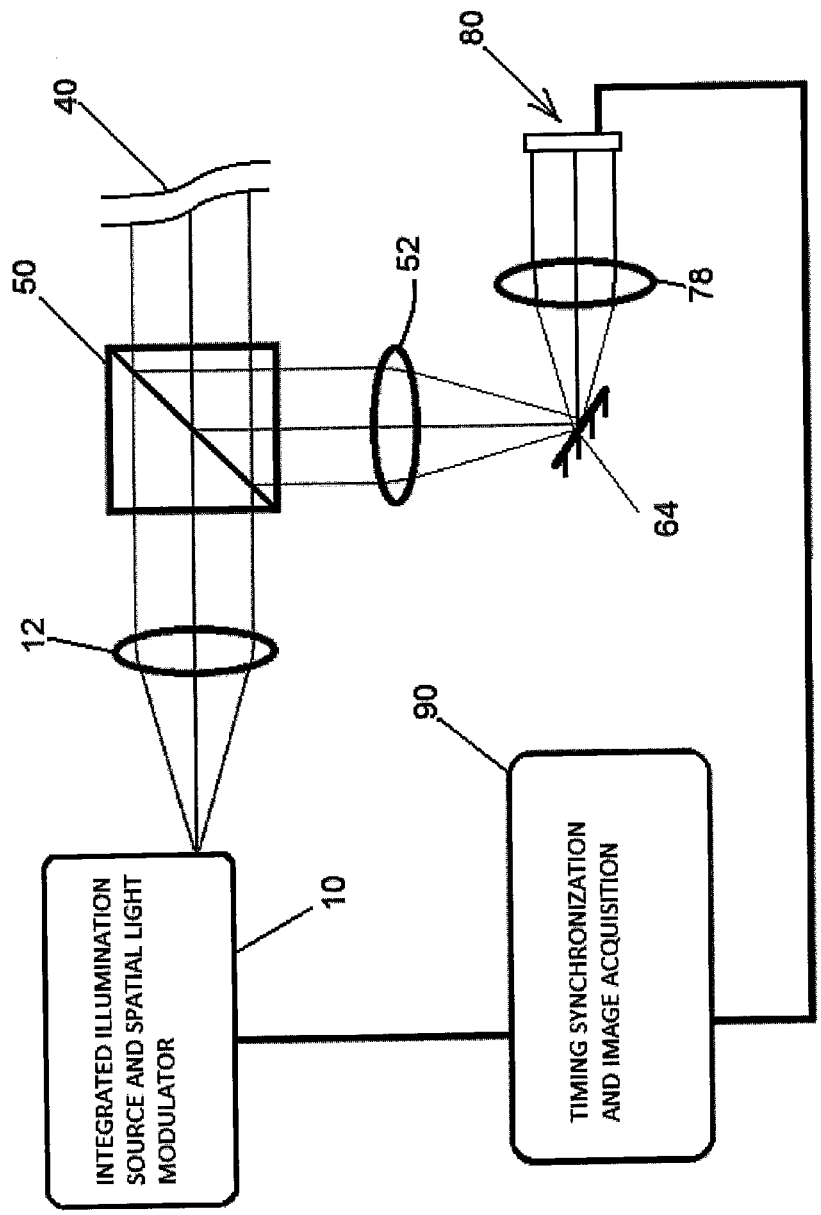
FIG. 6 is a schematic diagram of an adaptive optics confocal imaging device with simulated line scanning in accordance with the teachings of the present invention.

FIG. 6 is directed to another illustrative embodiment for performing confocal, adaptive optics, imaging of a target in accordance with the teachings of the present invention. In this embodiment, the integrated spatial light modulator and illumination source 10 produces a series of lines parallel to the rolling shutter on a 2-dimensional pixel array sensor 80. The lines are projected in rapid succession across the field of view of the target 40 to simulate line-scanning. In accordance with this illustrative embodiment, the integrated spatial light modulator and illumination source 10 is a compact and lightweight digital light projector (DLP), which can be handheld. A lens 12 is used to collimate the DLP output and set the focal plane of the target 40 to be conjugate to the micromirror array used in the DLP. A beamsplitter 50 directs a portion of the light return from the target 40 toward the sensor 80. An optical relay system, including lenses 52 and 78, adjusts the magnification between the target 40 and sensor 80 so that the illumination field of view approximately matches the active pixel region of interest on the sensor 80. The optical relay system also serves to set the focal plane of the sensor 80 to be conjugate to the target 40, and the micromirror array of the DLP illumination source 10. A deformable mirror wavefront controller 64 is placed in the Fourier plane of the sensor 80 to adjust the wavefront of the light return from the target 40. In accordance with this illustrative implementation of the invention, one or more portions of the acquired image are processed and used to provide feedback to the wavefront controller 64. Moreover, a video output signal driving the DLP illumination source 10 is filtered and used to externally trigger the sensor 80 to establish a substantially fixed spatial-temporal relationship between the illumination stripe and rolling shutter 90. Adjustments to any of the sensor's trigger delay, starting row or column, shutter width, or to the DLP stripe position and width allow precise software-based spatial-temporal alignment between the illumination stripe and rolling shutter position. It should be understood and appreciated by those of skill in the art that these attributes may be adjusted by a variety of control methods in real-time to perform calibration, or a variety of other embodiments, as described herein.

Figure 7:
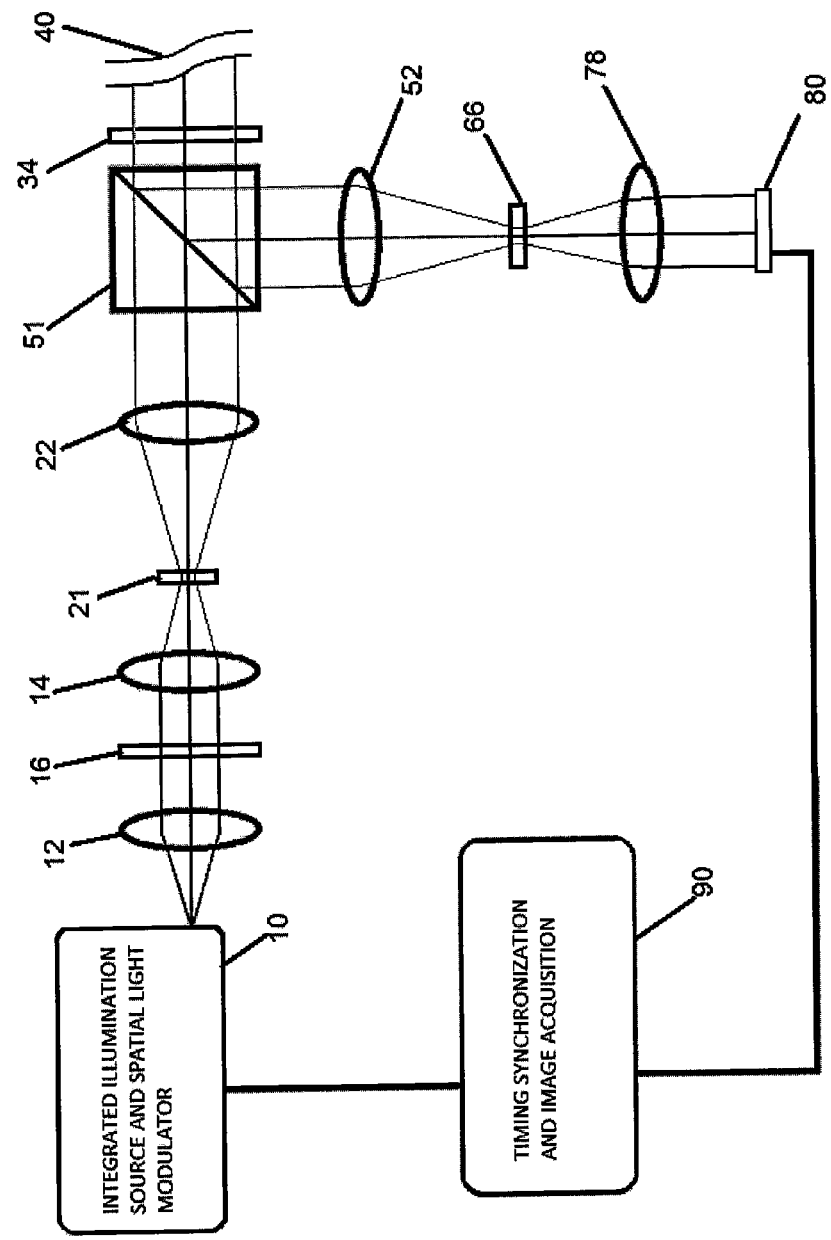
FIG. 7 is a schematic diagram of a confocal imaging device using spatial light modulation to adjust the phase and amplitude of the illumination and imaging light in accordance with the teachings of the present invention.

FIG. 7 shows one illustrative embodiment in which confocal imaging of a target using additional spatial light modulators to control the phase of the illumination and imaging light is performed in accordance with the teachings of the present invention. The integrated spatial light modulator and illumination source 10 produces a series of lines parallel to the rolling shutter on a 2-dimensional pixel array sensor 80. The lines are projected in rapid succession across the field of view of the target 40 to simulate line-scanning. In accordance with this illustrative embodiment, the integrated spatial light modulator and illumination source 10 is a compact and lightweight digital light projector (DLP), which can be handheld. Second 21 and third 66 spatial light modulators are arrays of liquid crystal elements placed in conjugate Fourier planes to the DLP micromirror array. An optical relay system, including lenses 12 and 14, adjusts the magnification of the Fourier plane, and a polarizer 16 is used to filter the illumination light to the axis of polarization that is retarded by the liquid crystal array 21. The elements of the liquid crystal array 21 are driven according to the spatio-temporal modulation pattern produced by the DLP illumination source 10. A lens 22 is used to collimate the illumination light and set the target focal plane 40 to be conjugate to the micromirror array used in the DLP illumination source 10. A birefringent material 34 is used to rotate the polarization of the illumination and light return from the target so that it is linearly polarized 90 degrees from the plane of polarization at the liquid crystal array 21. A polarizing beamsplitter 51 directs the light return from the target 40 toward the sensor 80. An optical relay system, including lenses 52 and 78, adjusts the magnification between the target 40 and sensor 80 so that the illumination field of view approximately matches the active pixel region of interest on the sensor 80. The optical relay system also serves to set the focal plane of the sensor 80 to be conjugate to the target 40, and the micromirror array of the DLP illumination source 10.

In accordance with certain aspects of the present invention, the second liquid crystal array 66 adjusts the phase of the light return from the target such that the elements of the liquid crystal array are driven according to the spatio-temporal position of the rolling shutter 80. In accordance with this specific illustrative implementation of the present invention, the acquired image is used to provide feedback to the liquid crystal arrays 21 and 66. A user may, in accordance with certain aspects of the present inventive embodiment, also explicitly set illumination and imaging phase maps for the liquid crystal arrays 21 and 66 through software.

In accordance with certain aspects of this illustrative embodiment, a video output signal driving the DLP illumination source 10 is filtered and used to externally trigger the sensor 80 to establish a substantially fixed spatial-temporal relationship between the illumination stripe and rolling shutter 90. Adjustments to any of the sensor's trigger delay, starting row or column, shutter width, or to the DLP stripe position and width allow precise software-based spatial-temporal alignment between the illumination stripe and rolling shutter position. It should be understood and appreciated by those of skill in the art that these attributes may be adjusted by a variety of control methods in real-time to perform calibration, or a variety of other embodiments, as described herein.

Figure 8:
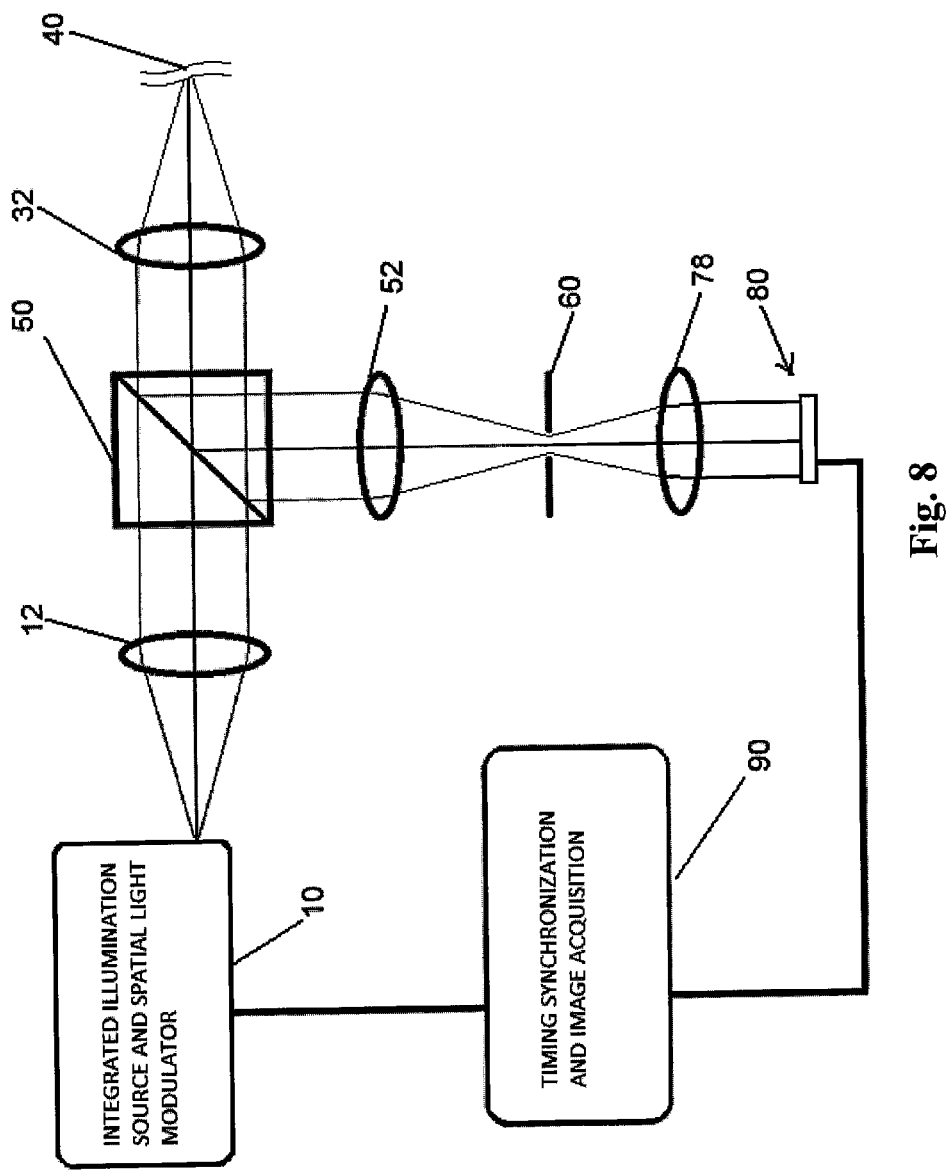
FIG. 8 is a schematic diagram of a confocal Fourier-Plane imaging device with angular-dependent spatial filtering in accordance with the teachings of the present invention.

In accordance with another aspect of the present invention, FIG. 8 depicts an illustrative embodiment in which angular-dependent confocal imaging of a target is performed. Here, the integrated spatial light modulator and illumination source 10 produces a series of lines parallel to the rolling shutter on a 2-dimensional pixel array sensor 80. The lines are projected in rapid succession to simulate line-scanning. In accordance with certain aspects of this embodiment, the integrated spatial light modulator and illumination source 10 is a compact and lightweight digital light projector (DLP), which can be handheld. A lens 12 is used to collimate the DLP output and a lens 32 is used to set the focal plane of the target 40 to be in a Fourier plane of the micromirror array used in the DLP. A beamsplitter 50 is used to direct a portion of light return from the target 40 toward the sensor 80. An optical relay system, including lenses 52 and 78, adjusts the magnification between the illumination pattern produced by the DLP illumination source 10 and the active pixel region of interest on the sensor 80. The optical relay system also serves to set the sensor focal plane 80 to be in a Fourier plane with respect to the target 40, and in a plane conjugate to the micromirror array of the DLP illumination source 10. An aperture stop 60 is optionally placed in the Fourier plane of the sensor 80 to reduce unwanted scattering, reflections, or light from the surrounding environment from reaching the sensor 80.

In accordance with one illustrative embodiment, the spatial filtering provided by the rolling shutter detects a limited angular range of light returning from the target 40. Specifically, the target 40 may be translated on a stage to image multiple regions of interest, and the video output signal driving the DLP illumination source 10 is filtered and used to externally trigger the sensor 80 to establish a substantially fixed spatial-temporal relationship between the illumination stripe and rolling shutter 90. Adjustments to any of the sensor's trigger delay, starting rolling shutter position, shutter width, or to the DLP stripe position and width allow precise software-based spatial-temporal alignment between the illumination stripe and rolling shutter position. It should be understood and appreciated by those of skill in the art that these attributes may be adjusted by a variety of control methods in real-time to perform calibration, or a variety of other embodiments, as described herein.

Figure 9:
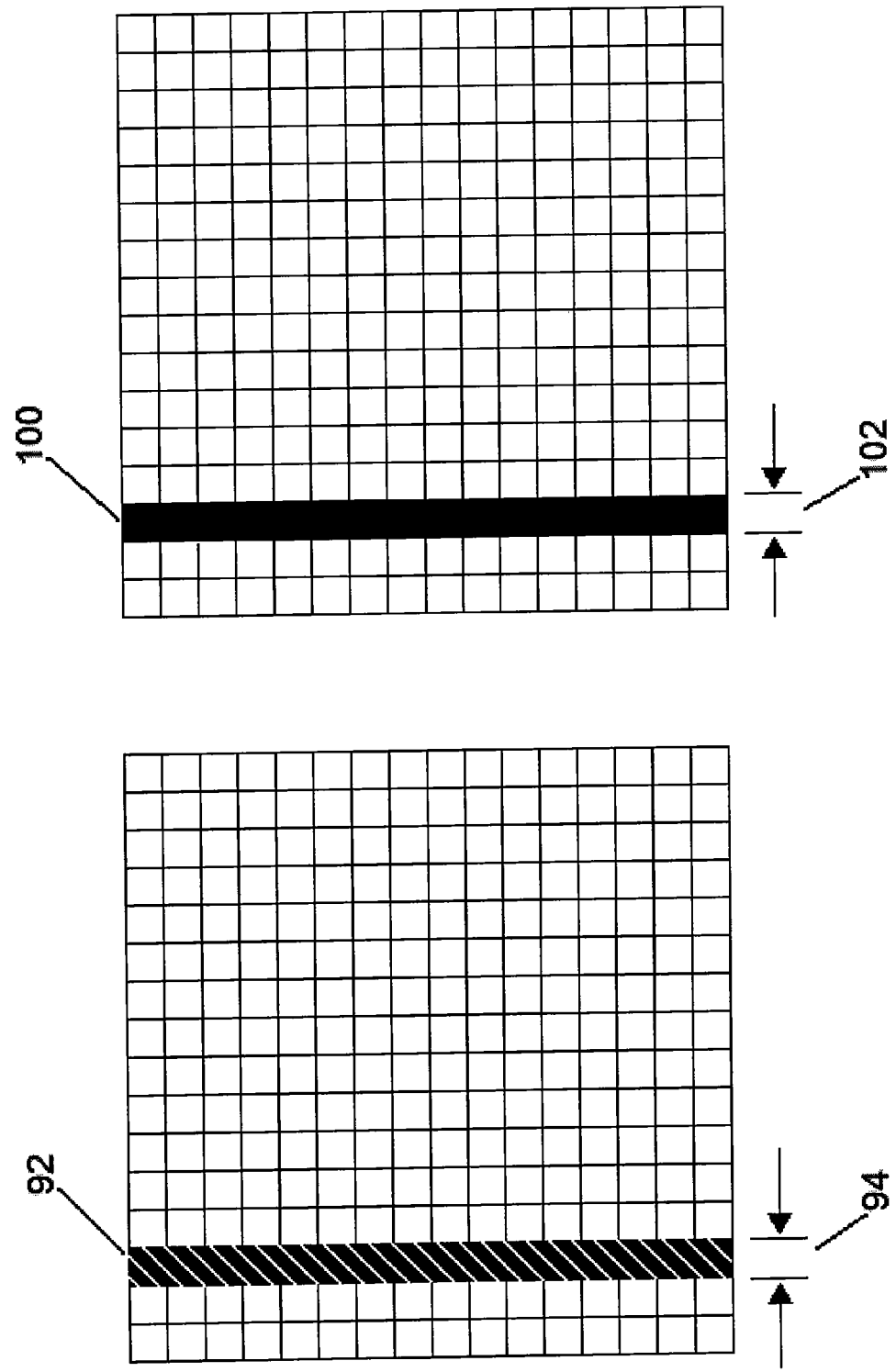
FIG. 9 depicts an intra-frame rolling shutter and illumination position for confocal imaging in accordance with teachings of the present invention.

FIG. 9 is a representative schematic of the spatial relationship between the modulation pattern at a target 92 and rolling shutter 100 on the sensor at a conjugate focal plane at an instant in time. While the illumination stripe width 94 and shutter width 102 are not necessarily equal, in accordance with certain aspects of the invention, they are substantially overlapped for standard confocal imaging (see FIG. 1, for the optical design of one standard confocal imaging embodiment). In this schematic diagram, the rolling shutter 100 moves left-to-right across the sensor region of interest during a frame exposure in synchrony with the illumination stripe provided by the spatial light modulator at a target 92. The grid pattern is for reference only, and it should be understood and appreciated herein that it is quite possible that the number of pixels in spatial light modulator will not exactly match the number of pixels in a 2-dimensional sensor array.

Figure 10:
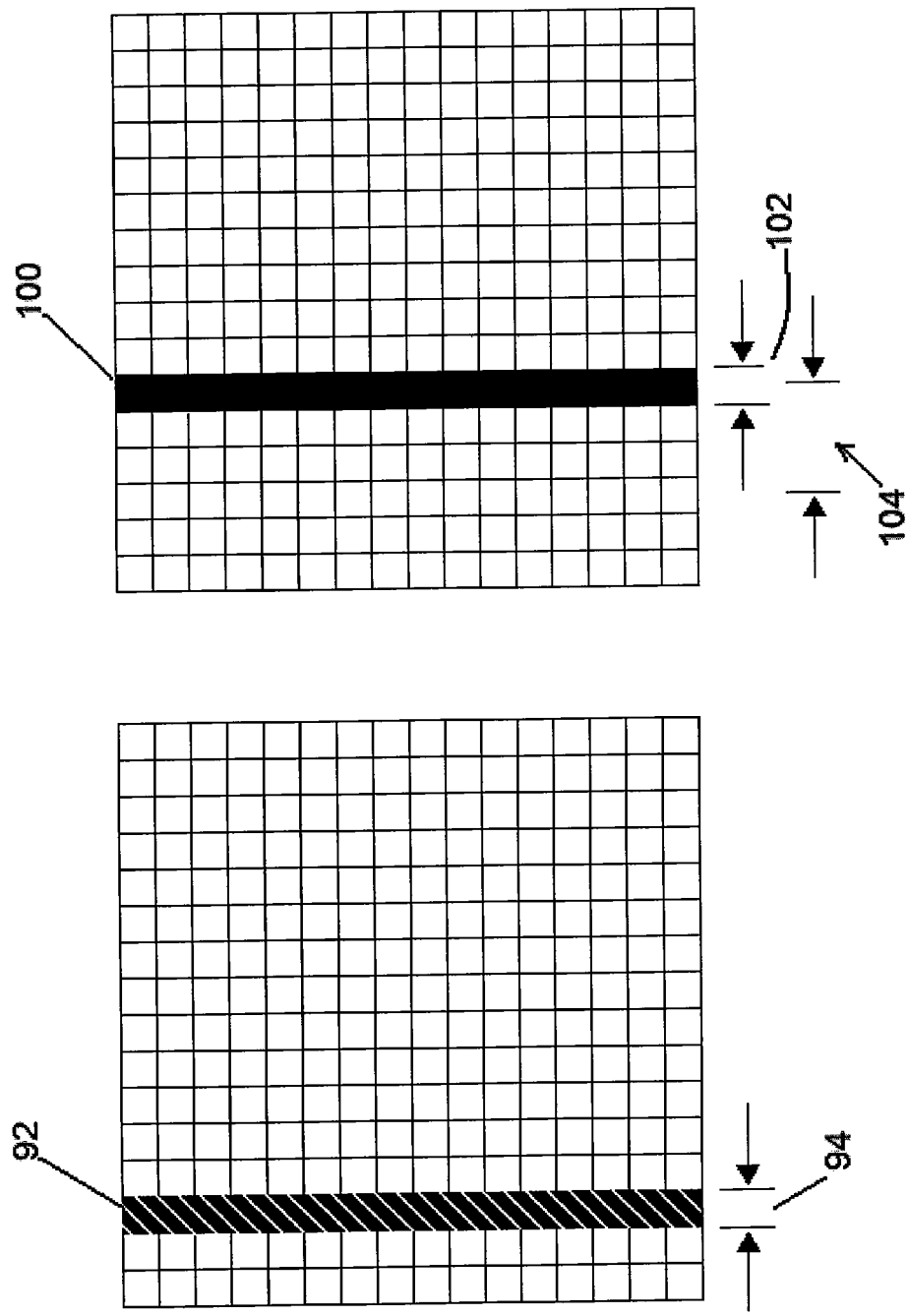
FIG. 10 depicts an intra-frame rolling shutter and illumination position for dark-field imaging in accordance with teachings of the present invention.

FIG. 10 is another representative schematic of the spatial relationship between the modulation pattern at a target 92 and a rolling shutter on the sensor at a conjugate focal plane 100 at an instant in time. The illumination stripe width 94 and shutter width 102 are not necessarily equal. In dark-field imaging embodiments, the stripe modulation pattern at a target 92 is spatially offset from the rolling shutter at a conjugate plane 100. In this schematic diagram, the rolling shutter 100 moves left-to-right across the sensor region of interest during a frame exposure in synchrony with the illumination stripe provided by the spatial light modulator at a target 92. The spatial offset 104 can be adjusted using the timing delay between the spatial light modulator and rolling shutter, or by adjusting the modulation pattern or pixel region of interest on the sensor as described herein. The grid pattern is for reference only, and it should be understood and appreciated herein that it is quite possible that the number of pixels in spatial light modulator will not exactly match the number of pixels in a 2-dimensional sensor array.

Figure 11:
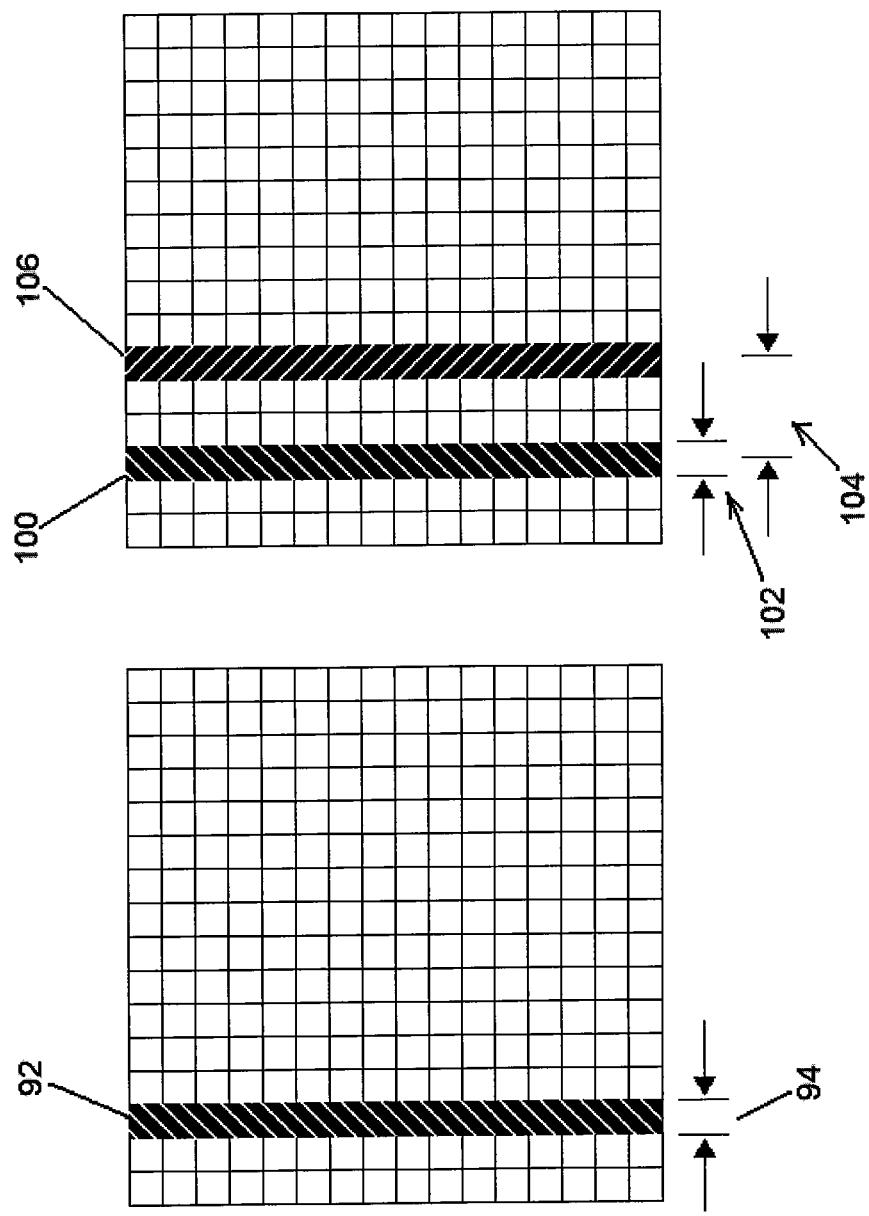
FIG. 11 depicts an intra-frame rolling shutter and illumination position for spatial filtering of polarization or spectral components of the imaging light in accordance with teachings of the present invention.

FIG. 11 is a representative schematic of the spatial relationship between the modulation pattern at a target 92 and rolling shutter 100 on the sensor at a conjugate focal plane at an instant in time. In this schematic diagram, the rolling shutter 100 moves left-to-right across the sensor region of interest during a frame exposure in synchrony with the illumination stripe provided by the spatial light modulator at a target 92. This schematic illustrates the spatial separation of the spectral or polarization components of the light returning from the target (see FIGS. 3 and 4, respectively). In accordance with these illustrative embodiments, a portion of the light return is dispersed or shifted in a direction perpendicular to the rolling shutter 106. The rolling shutter acts as a spatial filter; by adjusting the shutter width 102, spatial offset 104, or timing delay between the modulation pattern at a target 92 and rolling shutter 100, the user may filter the light return according to its polarization or spectral composition. The grid pattern is for reference only, and it should be understood and appreciated herein that it is quite possible that the number of pixels in spatial light modulator will not exactly match the number of pixels in a 2-dimensional sensor array.

Figure 12:
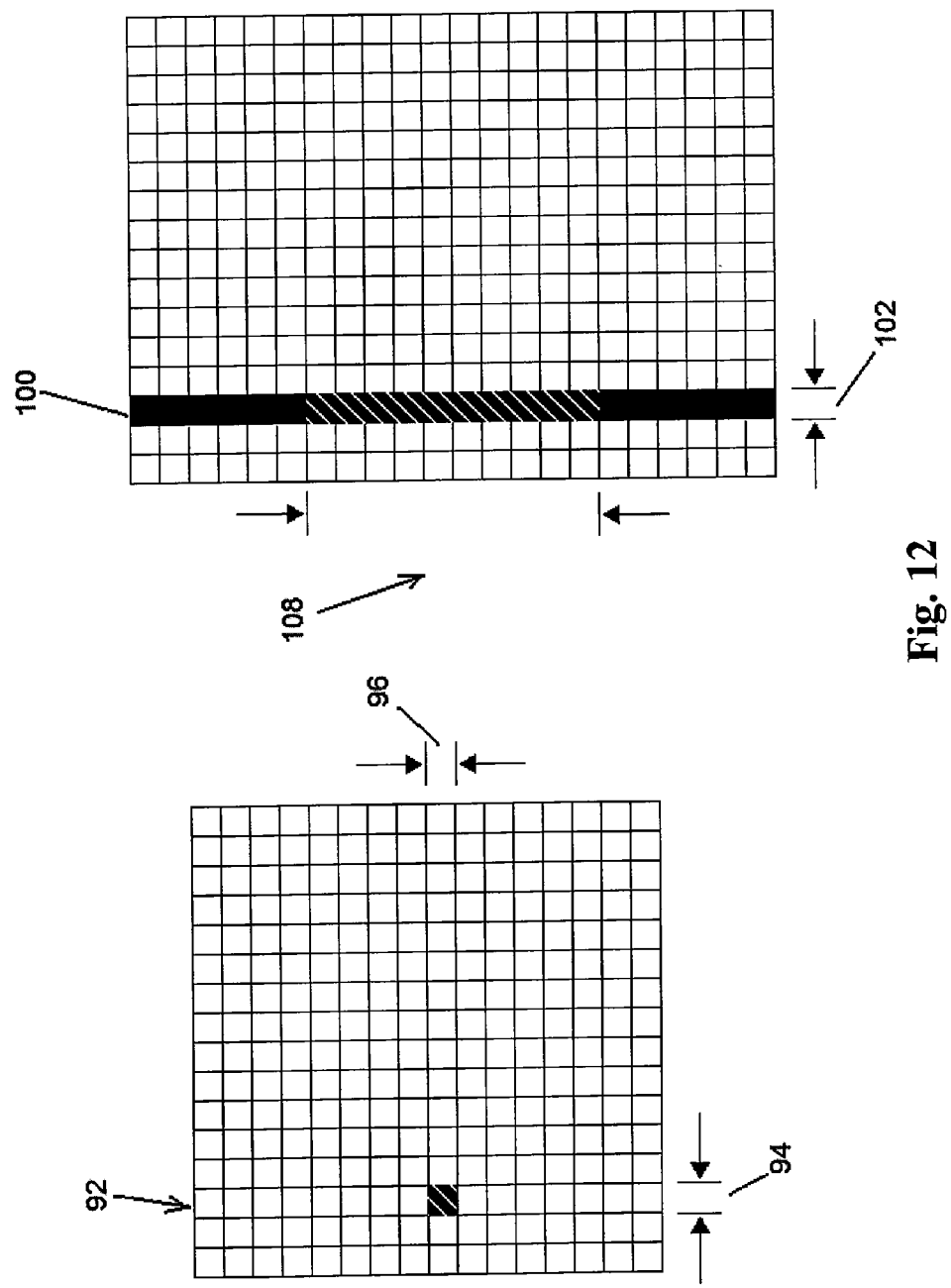
FIG. 12 depicts an intra-frame rolling shutter and illumination position for Spectral-Domain Optical Coherence Tomography Imaging in accordance with teachings of the present invention.

FIG. 12 is a representative schematic of the spatial relationship between the modulation pattern at a target 92 and rolling shutter 100 on the sensor at a conjugate focal plane at an instant in time. This illustrative schematic applies to various embodiments using spectral domain optical coherence tomography (SD-OCT) (see FIG. 5, for instance). In accordance with illustrative SD-OCT embodiments of the present invention, the spatial light modulator provides a point-like illumination at an instant in time. In this schematic diagram, the rolling shutter 100 moves left-to-right across the sensor region of interest during a frame exposure in synchrony with the illumination stripe provided by the spatial light modulator at a target 92. Each frame collects an OCT B-scan. The spectral content of the interferogram is dispersed in a direction parallel to the rolling shutter 100 shown by the cross-hatch region. The shutter width 102 is configured to spatially filter unwanted scattered light from outside the illumination focal area 94. The height of the dispersed interferogram 108, shown by the cross-hatch region, typically does not fill the entire length of the rolling shutter 100, shown in black. This arrangement allows B-scans to be recorded at different positions on the target by changing the modulation pattern at the target plane 92. The grid pattern is for reference only, and it should be understood and appreciated herein that it is quite possible that the number of pixels in spatial light modulator will not exactly match the number of pixels in a 2-dimensional sensor array.

FIG. 13 is a representative schematic of the spatial relationship between the modulation pattern at a target 92 and rolling shutter 100 on the sensor at a conjugate focal plane at an instant in time. This schematic applies to illustrative embodiments using dark field imaging and angularly resolved Fourier plane imaging (see FIG. 8, for instance) in accordance with the teachings of the present invention. In these illustrative embodiments, the rolling shutter is offset from the illumination. Moreover, in dark-field imaging embodiments, the use of two stripes with equal spatial offsets 104 on either side of the rolling shutter position 100 provides even illumination of the target. In the Fourier plane imaging embodiments, the illumination of the target at two angles and measurement at a single return angle, provides phase-sensitive information about the target that can be used to reconstruct its topography or depth range. In this schematic diagram, the rolling shutter 100 moves left-to-right across the sensor region of interest during a frame exposure in synchrony with the illumination stripe positions 96 and 97 provided by the spatial light modulator at a target 92. The spatial offset 104, stripe widths 94 and 95, shutter width 102 and stripe positions 96 and 97 can all be adjusted through software in real-time to construct an image. The grid pattern is for reference only, and it should be understood and appreciated herein that it is quite possible that the number of pixels in spatial light modulator will not exactly match the number of pixels in a 2-dimensional sensor array.

While an exemplary embodiment incorporating the principles of the present invention has been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A digital imaging device, comprising:
a digital light projector operable in a structured light illumination mode that is capable of converting a plurality of color or grayscale brightness values having a first frame rate to a limited number of brightness values having a second frame rate exceeding the first frame rate;
a pixel array detector having a rolling shutter functionality; and
at least one timing signal configured to control a spatial-temporal relationship between a rolling shutter of the pixel array detector and one or more illumination patterns provided by the digital light projector.

2. The device of claim 1, wherein the pixel array detector is a complementary metal-oxide semiconductor ("CMOS") sensor.

3. The device of claim 1, further comprising one or more additional digital light projectors.

4. The device of claim 1, wherein the rolling shutter of the pixel array detector is configured to perform at least one of the following filtering functions:
a) spatial filtering of at least one of light returning from a target and light passing through the target;
b) filtering at least one of the angle of light returning from the target and the angle of light passing through the target;
c) filtering spatially separated polarization components of at least one of light returning from the target and light passing through the target; and
d) filtering spatially separated frequency components of at least one of light returning from the target and light passing through the target.

5. The device of claim 4, further comprising an anisotropic material configured to spatially separate the polarization components of light returning from the target.

6. The device of claim 4, further comprising a dispersive component configured to spatially separate the frequency components of light returning from the target.

7. The device of claim 4, further comprising one or more additional pixel array detectors each having a rolling shutter functionality, wherein the one or more additional pixel array detectors each have a rolling shutter configured to perform one or more of the filtering functions.

8. The device of claim 4, further comprising a wavefront controller configured to modify a wavefront of light returning from a target.

9. The device of claim 1, further comprising one or more apertures or filters configured to at least partially restrict light traveling from the digital light projector to a target or light traveling from the target to the pixel array detector.

10. A method for digital imaging, the method comprising the steps of:
operating a digital light projector in a structured illumination mode to produce one or more illumination patterns during a frame exposure of a pixel array detector having a rolling shutter functionality, wherein the structured light illumination mode is capable of converting a plurality of color or grayscale brightness values having a first frame rate to a limited number of brightness values having a second frame rate exceeding the first frame rate;

directing light from the produced one or more illumination patterns onto a target;

directing light from the target to the pixel array detector having rolling shutter functionality; and using at least one timing signal to control a spatial-temporal relationship between a rolling shutter of the pixel array detector and the one or more illumination patterns provided by the digital light projector.

11. The method of claim 10, further comprising using the rolling shutter of the pixel array detector to perform at least one of the following filtering functions:
   a) spatial filtering of at least one of light returning from the target and light passing through the target;
   b) filtering at least one of the angle of light returning from the target and the angle of light passing through the target;
   c) filtering spatially separated polarization components of at least one of light returning from the target and light passing through the target; and
   d) filtering spatially separated frequency components of at least one of light returning from the target and light passing through the target.

12. The method of claim 11, further comprising using an anisotropic material to spatially separate the polarization components of light returning from the target.

13. The method of claim 11, further comprising using a dispersive component to spatially separate the frequency components of light returning from the target.

14. The method of claim 11, further comprising using one or more additional pixel array detectors each having a rolling shutter functionality to perform one or more of the filtering functions.

15. The method of claim 10, wherein the step of directing the produced one or more illumination patterns onto the target comprises establishing a known relationship between an illumination pattern and the angle of light directed onto the target.

16. The method of claim 10, wherein the step of directing light from the target to the pixel array detector comprises directing light from the target to a complementary metal-oxide semiconductor ("CMOS") sensor with rolling shutter functionality.

17. The method of claim 10, wherein a portion of light being directed from the digital light projector to the target is directed to a reference pathway of known optical path length.

18. The method of claim 17, wherein a portion of light from the reference pathway is directed to the pixel array detector.

19. The method of claim 10, further comprising using a wavefront controller to modify a wavefront of light returning from the target.

20. The method of claim 19, wherein a portion of light directed from the target to the pixel array detector is directed to a wavefront detector.

21. The method of claim 20, further comprising using wavefront data obtained by the wavefront detector to modify the wavefront of light returning from the target using the wavefront controller.

22. The method of claim 10, further comprising using image data obtained by the pixel array detector to adjust one or more of the following:
   (a) an illumination pattern produced by the digital light projector;
   (b) timing synchronization between the illumination pattern and the rolling shutter of the pixel array detector;
   (c) operating parameters of the pixel array detector, the operating parameters being selected from frame rate, gain, rolling shutter width and pixel region of interest; and
   (d) operating parameters of one or more light sources, the operating parameters being selected from driving current, driving frequency, driving phase, driving pulse width, and duty cycle.

23. A method for digital imaging, the method comprising the steps of:
   illuminating a spatial light modulator with one or more light sources, the illuminated spatial light modulator producing one or more modulation patterns during a frame exposure of a pixel array detector having a rolling shutter functionality;
   directing light from the produced one or more modulation patterns onto a target;
   directing light from the target to the pixel array detector having rolling shutter functionality;
   using at least one timing signal to control a spatial-temporal relationship between a rolling shutter of the pixel array detector and the one or more modulation patterns provided by the spatial light modulator;
   using a wavefront controller to modify a wavefront of light returning from the target; and
   using image data obtained by the pixel array detector to modify the wavefront of light returning from the target using the wavefront controller.

* * * * *